(12) United States Patent
Rajan et al.

(10) Patent No.: US 12,422,343 B2
(45) Date of Patent: Sep. 23, 2025

(54) APPARATUS, SYSTEMS, AND METHODS FOR PREPARING AN OUTPUT SAMPLE COMPRISING A DEFINED CONCENTRATION OF AN INFECTIOUS AGENT FOR DOWNSTREAM TESTING

(71) Applicant: Avails Medical, Inc., Menlo Park, CA (US)

(72) Inventors: Nitin K. Rajan, Palo Alto, CA (US); Andrew H. Theiss, Mountain View, CA (US); Oren S. Knopfmacher, San Francisco, CA (US); Meike Herget, Woodside, CA (US); Mathias Wipf, Basel (CH)

(73) Assignee: Avails Medical, Inc., Menlo Park, CA (US)

(*) Notice: Subject to any disclaimer, the term of this patent is extended or adjusted under 35 U.S.C. 154(b) by 970 days.

(21) Appl. No.: 16/430,266

(22) Filed: Jun. 3, 2019

(65) Prior Publication Data

US 2019/0293529 A1   Sep. 26, 2019

Related U.S. Application Data

(63) Continuation-in-part of application No. PCT/US2018/064093, filed on Dec. 5, 2018.

(60) Provisional application No. 62/597,657, filed on Dec. 12, 2017, provisional application No. 62/594,838, filed on Dec. 5, 2017.

(51) Int. Cl.
| | |
|---|---|
| *G01N 1/38* | (2006.01) |
| *C12Q 1/24* | (2006.01) |
| *G01N 27/00* | (2006.01) |
| *G01N 27/416* | (2006.01) |

(52) U.S. Cl.
CPC .............. *G01N 1/38* (2013.01); *C12Q 1/24* (2013.01); *G01N 27/00* (2013.01); *G01N 27/4167* (2013.01); *G01N 27/4168* (2013.01)

(58) Field of Classification Search
CPC ...... G01N 1/38; G01N 27/00; G01N 27/4167; G01N 27/4168; C12Q 1/24
See application file for complete search history.

(56) References Cited

U.S. PATENT DOCUMENTS

| | | | |
|---|---|---|---|
| 3,743,581 A | 7/1973 | Cady et al. | |
| 4,200,493 A | 4/1980 | Wilkins et al. | |
| 4,209,586 A | 6/1980 | Noller | |
| 4,236,893 A | 12/1980 | Rice | |
| 4,314,821 A | 2/1982 | Rice | |
| 4,321,322 A | 3/1982 | Ahnell | |
| 4,448,534 A | 5/1984 | Wertz et al. | |
| 4,615,978 A | 10/1986 | Sandine et al. | |
| 4,735,906 A | 4/1988 | Bastiaans | |
| 4,767,719 A | 8/1988 | Finlan | |
| 4,789,804 A | 12/1988 | Karube et al. | |
| 4,822,566 A | 4/1989 | Newman | |
| 4,965,193 A | 10/1990 | Chen | |
| 4,977,247 A | 12/1990 | Fahnestock et al. | |
| 5,064,756 A | 11/1991 | Carr et al. | |
| 5,077,210 A | 12/1991 | Eigler et al. | |
| 5,111,221 A | 5/1992 | Fare et al. | |
| 5,172,332 A | 12/1992 | Hungerford et al. | |
| 5,182,005 A | 1/1993 | Schwiegk et al. | |
| 5,218,304 A | 6/1993 | Kinlen et al. | |
| 5,356,782 A | 10/1994 | Moorman et al. | |
| 5,447,845 A | 9/1995 | Chu et al. | |
| 5,821,399 A | 10/1998 | Zelin | |
| 5,922,537 A | 7/1999 | Ewart et al. | |
| 6,280,586 B1 | 8/2001 | Wolf et al. | |
| 6,368,795 B1 | 4/2002 | Hefti | |
| 6,391,558 B1 | 5/2002 | Henkens et al. | |

(Continued)

FOREIGN PATENT DOCUMENTS

| | | |
|---|---|---|
| CN | 101057143 | 10/2007 |
| CN | 101852765 A | 10/2010 |
| CN | 105473740 | 4/2016 |
| CN | 107205808 | 9/2017 |
| EP | 0235024 | 9/1987 |
| EP | 1460130 | 9/2004 |
| EP | 2172767 | 4/2010 |
| JP | 1988-066454 | 3/1988 |
| JP | 1996-0886771 | 4/1996 |
| JP | 2002-112761 | 4/2002 |
| JP | 2003-052392 | 2/2003 |
| JP | 2005-287452 | 10/2005 |
| JP | 2006-511818 | 4/2006 |

(Continued)

OTHER PUBLICATIONS

Dutton, PL. "Redox potentiometry: determination of midpoint potentials of oxidation-reduction components of biological electron-transfer systems." Methods in Enzymology 1978, vol. 54, pp. 411-435. (Year: 1978).*

(Continued)

*Primary Examiner* — Melenie L Gordon
*Assistant Examiner* — Deepa Mishra
(74) *Attorney, Agent, or Firm* — Levine Bagade Han LLP

(57) ABSTRACT

Various methods, devices, and systems for preparing an output sample of a defined concentration are disclosed. The output sample can be used for downstream tests such as downstream anti-infective or antibiotic susceptibility testing (AST). The method can comprise diluting an aliquot of a source sample comprising an infectious agent to yield a diluted sample; exposing one or more sensors to the diluted sample, wherein at least a part of each of the one or more sensors is in fluid communication with the diluted sample; incubating the diluted sample at an incubation temperature; monitoring a change in a solution characteristic of the diluted sample using a parameter analyzer or a computing device coupled to the one or more sensors; and cooling the diluted sample to a cooling temperature when the concentration of infectious agents within the diluted sample reaches the defined concentration to yield the output sample.

10 Claims, 11 Drawing Sheets

(56) References Cited

U.S. PATENT DOCUMENTS

| | | |
|---|---|---|
| 6,391,577 B1 | 5/2002 | Mikkelsen et al. |
| 6,548,263 B1 | 4/2003 | Kapur et al. |
| 6,548,311 B1 | 4/2003 | Knol |
| 6,780,307 B2 | 8/2004 | Kidwell |
| 6,863,792 B1 | 3/2005 | Madou et al. |
| 7,745,272 B2 | 6/2010 | Van De Walle et al. |
| 8,508,100 B2 | 8/2013 | Lee et al. |
| 8,728,844 B1 | 5/2014 | Liu et al. |
| 9,377,456 B1 | 6/2016 | Herget et al. |
| 9,702,847 B2 | 7/2017 | Herget et al. |
| 9,766,201 B2 | 9/2017 | Herget et al. |
| 9,944,969 B2 | 4/2018 | Knopfmacher et al. |
| 9,963,733 B2 | 5/2018 | Knopfmacher et al. |
| 10,060,916 B2 | 8/2018 | Knopfmacher |
| 10,174,356 B2 | 1/2019 | Knopfmacher et al. |
| 10,254,245 B2 | 4/2019 | Knopfmacher et al. |
| 11,385,200 B2 * | 7/2022 | Knopfmacher .... G01N 27/4168 |
| 11,655,494 B2 * | 5/2023 | Knopfmacher .... G01N 27/4168 435/32 |
| 2002/0127623 A1 | 9/2002 | Minshull et al. |
| 2003/0073071 A1 | 4/2003 | Fritz et al. |
| 2003/0109056 A1 | 6/2003 | Vossmeyer et al. |
| 2003/0119208 A1 | 6/2003 | Yoon et al. |
| 2004/0195098 A1 | 10/2004 | Broadley et al. |
| 2005/0116263 A1 | 6/2005 | Lu et al. |
| 2006/0088839 A1 | 4/2006 | Matsui et al. |
| 2006/0102935 A1 | 5/2006 | Yitzchaik et al. |
| 2006/0197118 A1 | 9/2006 | Migliorato et al. |
| 2006/0246426 A1 | 11/2006 | Woodbury et al. |
| 2006/0286548 A1 | 12/2006 | Liposky |
| 2007/0037225 A1 | 2/2007 | Metzger et al. |
| 2007/0054396 A1 | 3/2007 | Peppers et al. |
| 2007/0072187 A1 | 3/2007 | Blok et al. |
| 2008/0012007 A1 | 1/2008 | Li et al. |
| 2008/0199863 A1 | 8/2008 | Haake et al. |
| 2009/0008247 A1 | 1/2009 | Chen et al. |
| 2009/0020438 A1 | 1/2009 | Hodges |
| 2009/0273354 A1 | 11/2009 | Dhirani et al. |
| 2010/0025660 A1 | 2/2010 | Jain et al. |
| 2010/0137143 A1 | 6/2010 | Rothberg et al. |
| 2010/0194409 A1 | 8/2010 | Gao et al. |
| 2011/0068372 A1 | 3/2011 | Ren et al. |
| 2011/0306032 A1 | 12/2011 | Galiano et al. |
| 2012/0032235 A1 | 2/2012 | Bikumandla |
| 2012/0077692 A1 | 3/2012 | Hassibi et al. |
| 2012/0088682 A1 | 4/2012 | Rothberg et al. |
| 2012/0143027 A1 | 6/2012 | Phillips et al. |
| 2012/0153262 A1 | 6/2012 | Paranjape et al. |
| 2012/0153407 A1 | 6/2012 | Chang et al. |
| 2012/0165246 A1 | 6/2012 | Lindner et al. |
| 2012/0168306 A1 | 7/2012 | Hassibi et al. |
| 2012/0208291 A1 | 8/2012 | Davis et al. |
| 2012/0214172 A1 | 8/2012 | Chen et al. |
| 2012/0256166 A1 | 10/2012 | Chen et al. |
| 2012/0261274 A1 | 10/2012 | Rearick et al. |
| 2012/0279859 A1 | 11/2012 | Rothberg et al. |
| 2013/0089883 A1 | 4/2013 | Dallenne et al. |
| 2013/0089932 A1 | 4/2013 | Wu et al. |
| 2013/0096013 A1 | 4/2013 | Esfandyarpour et al. |
| 2013/0105868 A1 | 5/2013 | Kalnitsky et al. |
| 2013/0217063 A1 | 8/2013 | Metzger et al. |
| 2014/0011218 A1 | 1/2014 | Han et al. |
| 2014/0057339 A1 | 2/2014 | Esfandyarpour et al. |
| 2014/0134656 A1 | 5/2014 | Dortet et al. |
| 2014/0186215 A1 | 7/2014 | Shinta et al. |
| 2014/0191294 A1 | 7/2014 | Bikumandla et al. |
| 2014/0231256 A1 | 8/2014 | Packingham et al. |
| 2014/0349005 A1 | 11/2014 | Everett et al. |
| 2015/0355129 A1 | 12/2015 | Knopfmacher |
| 2016/0039657 A1 | 2/2016 | Jain et al. |
| 2016/0068417 A1 | 3/2016 | Buschmann |
| 2016/0187332 A1 | 6/2016 | Herget et al. |
| 2016/0187334 A1 | 6/2016 | Herget et al. |
| 2016/0208306 A1 | 7/2016 | Pollak et al. |
| 2016/0209356 A1 | 7/2016 | Herget et al. |
| 2016/0266102 A1 | 9/2016 | Knopfmacher |
| 2017/0058313 A1 * | 3/2017 | Knopfmacher .......... C12Q 1/18 |
| 2017/0059508 A1 | 3/2017 | Knopfmacher et al. |
| 2017/0212075 A1 | 7/2017 | Knopfmacher et al. |
| 2017/0336348 A1 | 11/2017 | Herget et al. |
| 2017/0336384 A1 | 11/2017 | Ino et al. |
| 2017/0342459 A1 | 11/2017 | Knopfmacher et al. |
| 2018/0195106 A1 | 7/2018 | Knopfmacher et al. |
| 2018/0364221 A1 | 12/2018 | Knopfmacher |
| 2019/0046984 A1 | 2/2019 | Kelley et al. |
| 2019/0136290 A1 | 5/2019 | Knopfmacher et al. |
| 2019/0310214 A1 | 10/2019 | Herget et al. |
| 2020/0150082 A1 | 5/2020 | Knopfmacher et al. |
| 2020/0224241 A1 | 7/2020 | Knopfmacher et al. |
| 2021/0325371 A1 | 10/2021 | Rajan et al. |
| 2022/0317087 A1 | 10/2022 | Knopfmacher et al. |
| 2023/0250463 A1 | 8/2023 | Knopfmacher et al. |

FOREIGN PATENT DOCUMENTS

| | | |
|---|---|---|
| JP | 2011-58900 | 3/2011 |
| JP | 2011-062195 | 3/2011 |
| JP | 2012-024085 | 2/2012 |
| JP | 2011-085038 | 11/2012 |
| WO | WO 1992/009700 | 6/1992 |
| WO | WO 2003/044530 | 5/2003 |
| WO | WO 2003/052097 | 6/2003 |
| WO | WO 2004/077052 | 9/2004 |
| WO | WO 2006/102695 | 10/2006 |
| WO | WO 2007/035814 | 3/2007 |
| WO | WO 2009/021908 | 2/2009 |
| WO | WO 2010/062001 | 6/2010 |
| WO | WO 2012/078340 | 6/2012 |
| WO | WO 2013/096404 | 6/2013 |
| WO | WO 2014/080292 | 5/2014 |
| WO | WO 2014/134431 | 9/2014 |
| WO | WO 2015/077632 | 5/2015 |
| WO | WO 2015/188002 | 12/2015 |
| WO | WO 2016/005743 | 1/2016 |
| WO | WO 2016/028233 | 2/2016 |
| WO | WO 2016/044417 | 3/2016 |
| WO | WO 2016/061453 | 4/2016 |
| WO | WO 2016/065475 | 5/2016 |
| WO | WO 2016/109569 | 7/2016 |
| WO | WO 2017/035393 | 3/2017 |
| WO | WO 2017/107333 | 6/2017 |
| WO | WO 2017/132095 | 8/2017 |
| WO | WO 2017/209839 | 12/2017 |
| WO | WO 2018/111234 | 6/2018 |
| WO | WO 2018/145338 | 8/2018 |
| WO | WO 2019/005296 | 1/2019 |
| WO | WO 2019/070739 | 4/2019 |
| WO | WO 2019/113226 | 6/2019 |
| WO | WO 2019/246208 | 12/2019 |
| WO | WO 2020/117650 | 6/2020 |

OTHER PUBLICATIONS

Jiang et al. "A User-Friendly Robotic Sample Preparation Program for Fully Automated Biological Sample Pipetting and Dilution to Benefit the Regulated Bioanalysis", Journal of Laboratory Automation, 2012, vol. 17, No. 3, pp. 211-221. (Year: 2012).*

Rael et al. "Plasma Oxidation-Reduction Potential and Protein Oxidation in Traumatic Brain Injury", Journal of Neurotrauma, 2009, vol. 26, No. 8, pp. 1203-1211. (Year: 2009).*

Syal et al. "Current and emerging techniques for antibiotic susceptibility tests", Theranostics, 2017, vol. 7, Issue 7, pp. 1795-1805. (Year: 2017).*

Kang et al. "Survey of Redox-Active Moieties for Application in Multiplexed Electrochemical Biosensors", Anal. Chem., vol. 88, pp. 10452-10458, 2016.

Zuhri et al. 2016 (Effect of Methylene Blue Addition as a Redox Mediator on Performance of Microbial Desalination Cell by Utilizing Tempe Wastewater; International Journal of Technology 6: 952-961). (Year: 2016).

Oliu et al., "Impedimetric Sensors for Bacteria Detection," Biosensors—Micro and Nanoscale Applications, Chpt. 9 (Sep. 2015) p. 257-288.

(56) References Cited

OTHER PUBLICATIONS

Dutton 1978 (Redox potentiometry: Determination of midpoint potentials of oxidation-reduction components of biological electron-transfer systems; In Methods in Enzymology, 54:411-435) (Year: 1978).
Grossi Marco et al. "Bacterial concentration detection using a portable embedded sensor system for environmental monitoring", 2017 7th IEE International Workshop On Advances in Senors and Interfaces (IWASI), IEEE, Jun. 15, 2017, pp. 246-251.
Ivnitsky D et al: "Biosensors for Detection of Pathogenic Bacteria", Biosensors and Bioelectronics, Elsevier Science Ltd. UK, Amsterdam, NL, vol. 14, No. 7, Oct. 1, 1999, pp. 599-624.
J. Parce et al: "Detection of cell-affecting agents with a silicon biosensor", SCIENCE, vol. 246, No. 4927, Oct. 13, 1989 (Oct. 13, 1989), pp. 243-247.
Wan et al., 2011 (Impedimetric immunosensor doped with reduced graphene sheets fabricated by controllable electrodeposition for the non-labelled detection of bacteria; Biosensors and Bioelectronics 26 (2011) 1959-1964). (Year: 2011).
Yu Allen C et al: "Moni tori ng bacterial growth using tunable resistive pulse sensing with a pore-based technique11 , Applied Microbiology and Biotechnology, Springer Berlin Heidelberg, Berlin/Heidelberg, vol. 98, No. 2, Nov. 29, 2013, pp. 855-862.
Zhang, Xuzhi et al.: Online Monitoring of Bacterial Growth with an Electrical Sensor11 , Analytical Chemistry, vol. 90, No. 10, Apr. 24, 2018 (Apr. 24, 2018), pp. 6006-6011.
Zhou, Yong-Jun et al.: Real-time Detection System for Amount of Bacteria Based on an Electrochemical Sensor, Instrument Technique and Sensor, vol. 2, No. 2, Feb. 28, 2014 (Feb. 28, 2014), pp. 71-72 and 86.
Kazuo Iwata, Akira Matsuda, Effect of Mixed Culture of Redox Potentials of Candida and Various Bacteria, Sep. 1962, Fungus and Fungus Disease, vol. 3, No. 2, pp. 56-60 [TMI comments: English counterpart is not available].
Kazuo Iwata, Akira Matsuda, Effect of Mixed Culture of Redox Potentials of Candida and Various Bacteria, Sep. 1962, Fungus and Fungus Disease, vol. 3, No. 2, pp. 56-60.
"MINIFOR Laboratory Fermentor—Bioreactor", pp. 1-7, Feb. 24, 2017, Retrieved from the Internet: https://www.fermenter.net/pdf/LAMBDA_MINIFOR_laboratory_fermentor_description.pdf.
Ingraham 1933 (The Bacteriostatic Action of Gentian Violet and its Dependence on the Oxidation-Reduction Potential; Journal of Bacteriology, vol. XXVI, No. 6. p. 573-598) (Year: 1933).
Kotzian et al. 2007 (Oxides of platinum metal group as potential catalysts in carbonaceous amperometric biosensors based on oxidases; Sensors and Actuators B 124: 297-302). (Year: 2007).
Vila et al. 2016 (*Escherichia coli*: an old friend with new tidings; FEMS Microbiology Reviews; 40: 437-463). (Year: 2016).
Berney et al. "A DNA diagnostic biosensor: development, characterization and performance" Sensors and Actuators B: Chemical: International Journal Devoted To Research and Development of Physical and Chemical Transducers, Elsevier BV, NL, vol. 68, No. 1-3, Aug. 25, 2000, pp. 100-108.

Dortet, Laurent et al., "Bloodstream Infections Caused by *Pseudomonas* spp.: How To Detect Carbapenemase Producers Directly from Blood Cultures", Journal of Clinical Microbiology, 52(4):1269-1273, Apr. 2014.
Dortet, Laurent et al., "CarbAcineto NP Test for Rapid Detection of Carbapenemase- Producing *Acinetobacter* spp.", Journal of Clinical Microbiology, 52(7):2359-2364, Jul. 2014.
Dortet, Laurent et al., "Evaluation of the RAPIDECw CARBA NP, the Rapid CARB Screenw and the Carba NP test for biochemical detection of carbapenemase-producing Enterobacteriaceae", J Antimicrob Chemother, 70:3014-3022, 2015.
Dortet, Laurent et al., "Further Proofs of Concept for the Carba NP Test", Antimicrobial Agents and Chemotherapy, 58(2):1269, Feb. 2014.
Dortet, Laurent et al., "Rapid Identification of Carbapenemase Types in Enterobacteriaceae and *Pseudomonas* spp. by Using a Biochemical Test", Antimicrobial Agents and Chemotherapy, 56(12):6437-6440, Dec. 2012.
Estrela, Pedro et al., "Label-Free Sub-picomolar Protein Detection with Field-Effect Transistors," Analytical Chemistry, vol. 82, No. 9, May 1, 2010, 3531-3536.
Hammock, Mallory L. et al., "Electronic readout ELISA with organic field-effect transistors as a prognostic test for preeclampsia," Advanced Materials, 26: 6138-6144. doi: 10.1002/adma.201401829 (Jul. 22, 2014).
Kumar et al., "Sensitivity Enhancement Mechanisms in Textured Dielectric Based Electrolyte-Insulator-Semiconductor (EIS) Sensors," *ECS Journal of Solid State Science and Technology*, 4(3):N18-N23 (2015).
Mathias, W. et al., "Selective Sodium Sensing with Gold-Coated Silicon Nanowire Field-Effect Transistors in a Differential Setup," ACS Nano 7, 5978-5983 (2013).
Nordmann, Patrice et al., "Strategies for identification of carbapenemase-producing Enterobacteriaceae", J Antimicrob Chemother, 68:487-489, 2013.
Poghossian et al., "Penicillin Detection by Means of Field-Effect Based Sensors: EnFET, Capacitive EIS Sensor or LAPS?", *Sensors and Actuators B*, 78:237 (2001).
Poirel, Laurent et al., "Rapidec Carba NP Test for Rapid Detection of Carbapenemase Producers", Journal of Clinical Microbiology, 53(9):3003-3008, Sep. 2015.
Pourciel-Gouzy M L et al: "pH-ChemFET-based analysis devices for the bacterial activity monitoring." Sensors and Actuators B: Chemical: International Journal Devoted To Research and Development of Physical and Chemical Transducers, Elsevier BV, NL, vol. 134, No. 1 Aug. 28, 2008, pp. 339-344.
Salm, Eric et al., "Electrical Detection of Nucleic Acid Amplification Using an On-Chip Quasi-Reference Electrode and a PVC REFET," dx.doi.org/10.1021/ac500897t, *Anal. Chem.*, 2014, 86, 6968-6975.
Schoning, Michael J., "'Playing Around' with Field-Effect Sensors on the Basis of EIS Structures, LAPS and ISFETs," *Sensors*, 5:126-138 (2005).

\* cited by examiner

| SMa CDC-27 LUT | | SMa CDC-91 LUT | | SMa CDC-99 LUT | |
|---|---|---|---|---|---|
| CONC (... x 1e8 CFU/mL) | pH (ΔpH) | CONC (... x 1e8 CFU/mL) | pH (ΔpH) | CONC (... x 1e8 CFU/mL) | pH (ΔpH) |
| 1 | 6.96 (-0.04) | 1 | 6.96 (-0.04) | 1 | 6.96 (-0.04) |
| 2 | 6.90 (-0.10) | 2 | 6.89 (-0.11) | 2 | 6.89 (-0.11) |
| 3 | 6.80 (-0.20) | 3 | 6.77 (-0.23) | 3 | 6.77 (-0.23) |
| 4 | 6.70 (-0.30) | 4 | 6.63 (-0.37) | 4 | 6.64 (-0.36) |
| 5 | 6.59 (-0.41) | 5 | 6.43 (-0.57) | 5 | 6.49 (-0.51) |

| SMa CDC-121 LUT | | SMa CDC-122 LUT | | SMa CDC-130 LUT | |
|---|---|---|---|---|---|
| CONC (... x 1e8 CFU/mL) | pH (ΔpH) | CONC (... x 1e8 CFU/mL) | pH (ΔpH) | CONC (... x 1e8 CFU/mL) | pH (ΔpH) |
| 1 | 6.97 (-0.03) | 1 | 6.97 (-0.03) | 1 | 6.94 (-0.06) |
| 2 | 6.89 (-0.11) | 2 | 6.92 (-0.08) | 2 | 6.89 (-0.11) |
| 3 | 6.76 (-0.24) | 3 | 6.81 (-0.19) | 3 | 6.79 (-0.21) |
| 4 | 6.54 (-0.46) | 4 | 6.66 (-0.34) | 4 | 6.67 (-0.33) |
| 5 | 6.35 (-0.65) | 5 | 6.51 (-0.49) | 5 | 6.54 (-0.46) |

| SMa Species-Specific LUT | |
|---|---|
| CONC (... x 1e8 CFU/mL) | Averaged pH (ΔpH) |
| 1 | 6.96 (-0.04) |
| 2 | 6.90 (-0.10) |
| 3 | 6.78 (-0.22) |
| 4 | 6.64 (-0.36) |
| 5 | 6.49 (-0.51) | pH AND REFERENCE SAMPLE CONCENTRATION AS A FUNCTION OF TIME FOR REFERENCE SAMPLE COMPRISING SMa CDC-27

| ECo PSC-18 ||
|---|---|
| CONC (N) (... x 1e8 CFU/mL) | ΔORP (mV) |
| 0.5 | -151 |
| 1.0 | -215 |
| 1.5 | -265 |
| 2.0 | -308 |
| 2.5 | -358 |

| ECo PSC-26 ||
|---|---|
| CONC (N) (... x 1e8 CFU/mL) | ΔORP (mV) |
| 0.5 | -107 |
| 1.0 | -185 |
| 1.5 | -226 |
| 2.0 | -261 |
| 2.5 | -272 |

| ECo PSC-66 ||
|---|---|
| CONC (N) (... x 1e8 CFU/mL) | ΔORP (mV) |
| 0.5 | -109 |
| 1.0 | -184 |
| 1.5 | -236 |
| 2.0 | -277 |
| 2.5 | -303 |

| ECo Species-Specific LUT ||
|---|---|
| CONC (N) (... x 1e8 CFU/mL) | ΔORP avg (mV) |
| 0.5 | -110 |
| 1.0 | -206 |
| 1.5 | -265 |
| 2.0 | -305 |
| 2.5 | -335 |

| ECo PSC-72 ||
|---|---|
| CONC (N) (... x 1e8 CFU/mL) | ΔORP (mV) |
| 0.5 | -25 |
| 1.0 | -156 |
| 1.5 | -256 |
| 2.0 | -334 |
| 2.5 | -396 |

| ECo CDC-13 ||
|---|---|
| CONC (N) (... x 1e8 CFU/mL) | ΔORP (mV) |
| 0.5 | -147 |
| 1.0 | -296 |
| 1.5 | -353 |
| 2.0 | -374 |
| 2.5 | -389 |

| ECo CDC-19 ||
|---|---|
| CONC (N) (... x 1e8 CFU/mL) | ΔORP (mV) |
| 0.5 | -118 |
| 1.0 | -200 |
| 1.5 | -254 |
| 2.0 | -274 |
| 2.5 | -293 |

APPARATUS, SYSTEMS, AND METHODS FOR PREPARING AN OUTPUT SAMPLE COMPRISING A DEFINED CONCENTRATION OF AN INFECTIOUS AGENT FOR DOWNSTREAM TESTING

This application is a continuation-in-part (CIP) of PCT Application No. PCT/US2018/064093 filed on Dec. 5, 2018, which claims the benefit of U.S. Provisional Application No. 62/597,657 filed on Dec. 12, 2017 and U.S. Provisional Application No. 62/594,838 filed on Dec. 5, 2017, the entireties of which are incorporated herein by reference.

TECHNICAL FIELD

The present disclosure relates generally to preparation of diagnostic samples and, more specifically, to apparatus, systems, and methods for preparing an output sample comprising a defined concentration of an infectious agent for downstream testing.

BACKGROUND

Infections caused by anti-infective resistant microorganisms or infectious agents are a significant problem for healthcare professionals in hospitals, nursing homes, and other healthcare environments. Rapid detection of the susceptibility of such infectious agents to antibiotics or other anti-infectives is crucial in order to prevent the spread of their resistance profiles. While new technologies (e.g., matrix-assisted laser desorption/ionization-time of flight mass spectrometry (MALDI-TOF MS), rapid polymerase chain reaction (rapid PCR), etc.) have been developed for identifying infectious agents in samples such as positive blood cultures, the first step in most testing protocols still involves preparation of an output sample comprising infectious agents at a defined concentration. For example, most anti-infective or antibiotic susceptibility testing (AST) protocols require the preparation of an output sample or inoculum having a concentration that matches a McFarland standard.

Existing methods and instruments used to prepare such output samples include costly, time-intensive (e.g., up to 24 hours), and labor-intensive microbial culturing techniques. However, those methods often require manual interpretation by skilled personnel and are prone to technical or clinician error. In addition, certain biological samples harboring infectious agents, such as samples containing animal or human blood, are often difficult to assess using prevailing optical techniques given the samples' opacity. Moreover, such optical techniques often require expensive equipment.

As a result of the above limitations and restrictions, there is a need for improved apparatus, systems, and methods to quickly and effectively prepare an output sample or standardized inoculum comprising a defined concentration of an infectious agent for downstream testing.

SUMMARY

Disclosed are various methods, devices, and systems for preparing an output sample of a defined concentration. In one embodiment, a method of preparing an output sample of a defined concentration is disclosed. The method comprises diluting an aliquot of a source sample comprising an infectious agent by a dilution factor to yield a diluted sample and exposing one or more sensors to the diluted sample. At least a part of each of the one or more sensors can be in fluid communication with the diluted sample when exposed to the diluted sample. The method can further comprise incubating the diluted sample at an incubation temperature. The diluted sample can be incubated when the one or more sensors are exposed to the diluted sample. The incubation temperature can be between about 33° C. and about 37° C.

The method can also comprise monitoring a change in a solution characteristic of the diluted sample using a parameter analyzer or a computing device coupled to the one or more sensors. The method can further comprise cooling the diluted sample to a cooling temperature when the solution characteristic of the diluted sample changes by a threshold amount to yield the output sample of the defined concentration. In some embodiments, the cooling temperature can be between about 4° C. and about 25° C.

The method can also comprise using one or more processors of a computing device coupled to the one or more sensors to retrieve a universal look-up table from a database prior to monitoring the change in the solution characteristic of the diluted sample. The one or more processors of the computing device can set the threshold amount based on the defined concentration, concentration data obtained from the universal look-up table, and solution characteristic data obtained from the universal look-up table. The universal look-up table can be generated from multiple strain-specific look-up tables representing data measured from multiple reference samples monitored over time. At least one of the multiple reference samples can comprise a reference infectious agent of a different species from the infectious agent in the source sample.

In some embodiments, each of the multiple strain-specific look-up tables can be generated by monitoring changes in the solution characteristic of a reference sample over a period of time, conducting sample enumeration assays of the reference sample over the same period of time, converting results of the sample enumeration assays to reference sample concentrations using a conversion factor, and associating the reference sample concentrations with the changes in the solution characteristic of the reference sample. The universal look-up table can be generated by taking an average of all solution characteristic change amounts obtained from the multiple strain-specific look-up tables for each of the reference sample concentrations and associating each of the reference sample concentrations with an averaged solution characteristic change amount. The sample enumeration assays can comprise optical density measurements, plate count assays, flow cytometry assays, or a combination thereof.

The method can further comprise retrieving a species-specific look-up table from a database based on a species of the infectious agent in the source sample prior to monitoring the change in the solution characteristic of the diluted sample and setting the threshold amount based on the defined concentration, concentration data obtained from the species-specific look-up table, and solution characteristic data obtained from the species-specific look-up table. The species-specific look-up table can be generated from multiple strain-specific look-up tables representing data obtained from multiple reference samples monitored over time. Each of the multiple reference samples can comprise a reference infectious agent of the same species as the infectious agent in the source sample.

Each of the multiple strain-specific look-up tables can be generated by monitoring changes in the solution characteristic of a reference sample over a period of time, conducting sample enumeration assays of the reference sample over the same period of time, converting results of the sample enumeration assays to reference sample concentrations using a conversion factor, and associating the reference sample concentrations with the changes in the solution characteristic of the reference sample. The species-specific look-up table can be generated by taking an average of all solution characteristic change amounts obtained from the multiple strain-specific look-up tables for each of the reference sample concentrations and associating each of the reference sample concentrations with an averaged solution characteristic change amount. In these embodiments, the sample enumeration assays can comprise optical density measurements, plate count assays, flow cytometry assays, or a combination thereof.

The method can further comprise diluting the output sample by another dilution factor to yield a further diluted sample. The further diluted sample can comprise an infectious agent concentration required for downstream testing.

In some embodiments, the solution characteristic can be an oxidation-reduction potential (ORP) and the one or more sensors can be ORP sensors. The ORP can be monitored in the absence of any added reporter molecules in the diluted sample. Each of the one or more ORP sensors can comprise a redox-active layer. Each of the one or more ORP sensors can comprise at least one of an active electrode and a reference electrode. In some embodiments, the redox-active layer can comprise a gold layer, a platinum layer, a metal oxide layer, a carbon layer, or a combination thereof.

In other embodiments, the solution characteristic can be pH and the one or more sensors can be pH sensors. Each of the one or more pH sensors can comprise a pH-sensitive layer. The pH can be monitored in the absence of any added reporter molecules in the diluted sample. Each of the one or more pH sensors can comprise at least one of an active electrode and a reference electrode. In some embodiments, the pH-sensitive layer can comprise an oxide layer, a silane layer, a self-assembled mono layer (SAM), a hydrogel layer, a protein layer, a polymer layer, or a combination thereof.

The source sample can comprise a bodily fluid, a wound swab or sample, a rectal swab or sample, another type of biological sample, a culture derived therefrom, or a combination thereof. The bodily fluid can comprise urine, blood, sputum, saliva, breast milk, spinal fluid, semen, vaginal secretions, synovial fluid, pleural fluid, peritoneal fluid, pericardial fluid, amniotic fluid, cultures of bodily fluid that have tested positive for infectious agent growth, or a combination thereof. The infectious agent can comprise bacteria, fungus, mold, or a combination thereof.

In another embodiment, a method of preparing an output sample of a defined concentration is disclosed. The method can comprise diluting an aliquot of a source sample comprising an infectious agent by a dilution factor to yield a diluted sample. The method can further comprise selecting a first threshold amount and a second threshold amount from a look-up table. The first threshold amount and the second threshold amount can represent changes in a solution characteristic of the diluted sample. The method can further comprise exposing one or more sensors to the diluted sample. At least a part of each of the one or more sensors can be in fluid communication with the diluted sample when exposed to the diluted sample. The method can also comprise incubating the diluted sample at an incubation temperature. The diluted sample can be incubated when the one or more sensors are exposed to the diluted sample.

The method can further comprise monitoring a change in the solution characteristic of the diluted sample using a parameter analyzer or a computing device coupled to the one or more sensors. The method can also comprise obtaining a first threshold time corresponding to an amount of time elapsed for the solution characteristic of the diluted sample to change by the first threshold amount and obtaining a second threshold time corresponding to the amount of time elapsed for the solution characteristic of the diluted sample to change by the second threshold amount. The method can further comprise determining a sample preparation time corresponding to the amount of time necessary for the infectious agent within the diluted sample to reach the defined concentration based on the first threshold time, the second threshold time, concentration data from the look-up table, and the defined concentration.

In another embodiment, a system for preparing an output sample of a defined concentration is disclosed. The system can comprise one or more fluid delivery conduits or metering conduits configured to dilute an aliquot of a source sample comprising an infectious agent by a dilution factor to yield a diluted sample. The system can also comprise one or more sensors. In some embodiments, the diluted sample can be delivered or otherwise introduced to the one or more sensors. In other embodiments, the one or more sensors can be exposed to the diluted sample by being positioned in fluid communication with the diluted sample.

The system can further comprise an incubating component configured to incubate the diluted sample at an incubation temperature. The diluted sample can be incubated when the one or more sensors are exposed to the diluted sample. The incubation temperature can be between about 33° C. and about 37° C.

The system can also comprise at least one of a parameter analyzer and a computing device coupled to the one or more sensors. One or more processors of the parameter analyzer or the computing device can monitor a change in a solution characteristic of the diluted sample using a parameter analyzer or a computing device coupled to the one or more sensors.

The system can further comprise a cooling component configured to cool the diluted sample to a cooling temperature when the solution characteristic of the diluted sample changes by a threshold amount to yield the output sample of the defined concentration. In some embodiments, the cooling temperature can be between about 4° C. and about 25° C.

The system can also comprise using the one or more processors of the computing device coupled to the one or more sensors to retrieve a universal look-up table from a database prior to monitoring the change in the solution characteristic of the diluted sample. The one or more processors of the computing device can set the threshold amount based on the defined concentration, concentration data obtained from the universal look-up table, and solution characteristic data obtained from the universal look-up table. The universal look-up table can be generated from multiple strain-specific look-up tables representing data measured from multiple reference samples monitored over time. At least one of the multiple reference samples can comprise a reference infectious agent of a different species from the infectious agent in the source sample.

In some embodiments, each of the multiple strain-specific look-up tables can be generated by monitoring changes in the solution characteristic of a reference sample over a period of time, conducting sample enumeration assays of the reference sample over the same period of time, converting results of the sample enumeration assays to reference sample concentrations using a conversion factor, and associating the reference sample concentrations with the changes in the solution characteristic of the reference sample. The universal look-up table can be generated by the one or more processors of the computing device by taking an average of all solution characteristic change amounts obtained from the multiple strain-specific look-up tables for each of the reference sample concentrations and associating each of the reference sample concentrations with an averaged solution characteristic change amount. The sample enumeration assays can comprise optical density measurements, plate count assays, flow cytometry assays, or a combination thereof.

The one or more processors of the computing device can also retrieve a species-specific look-up table from a database based on a species of the infectious agent in the source sample prior to monitoring the change in the solution characteristic of the diluted sample and set the threshold amount based on the defined concentration, concentration data obtained from the species-specific look-up table, and solution characteristic data obtained from the species-specific look-up table. The species-specific look-up table can be generated from multiple strain-specific look-up tables representing data obtained from multiple reference samples monitored over time. Each of the multiple reference samples can comprise a reference infectious agent of the same species as the infectious agent in the source sample.

Each of the multiple strain-specific look-up tables can be generated by monitoring changes in the solution characteristic of a reference sample over a period of time, conducting sample enumeration assays of the reference sample over the same period of time, converting results of the sample enumeration assays to reference sample concentrations using a conversion factor, and associating the reference sample concentrations with the changes in the solution characteristic of the reference sample. The species-specific look-up table can be generated by taking an average of all solution characteristic change amounts obtained from the multiple strain-specific look-up tables for each of the reference sample concentrations and associating each of the reference sample concentrations with an averaged solution characteristic change amount. In these embodiments, the sample enumeration assays can comprise optical density measurements, plate count assays, flow cytometry assays, or a combination thereof.

The system can further comprise using the one or more fluid delivery conduits or metering conduits to dilute the output sample by another dilution factor to yield a further diluted sample. The further diluted sample can comprise an infectious agent concentration required for downstream testing.

In some embodiments, the solution characteristic can be an oxidation-reduction potential (ORP) and the one or more sensors can be ORP sensors. The ORP can be monitored in the absence of any added reporter molecules in the diluted sample. Each of the one or more ORP sensors can comprise a redox-active layer. Each of the one or more ORP sensors can comprise at least one of an active electrode and a reference electrode. In some embodiments, the redox-active layer can comprise a gold layer, a platinum layer, a metal oxide layer, a carbon layer, or a combination thereof.

In other embodiments, the solution characteristic can be pH and the one or more sensors can be pH sensors. Each of the one or more pH sensors can comprise a pH-sensitive layer. The pH can be monitored in the absence of any added reporter molecules in the diluted sample. Each of the one or more pH sensors can comprise at least one of an active electrode and a reference electrode. In some embodiments, the pH-sensitive layer can comprise an oxide layer, a silane layer, a self-assembled mono layer (SAM), a hydrogel layer, a protein layer, a polymer layer, or a combination thereof.

The source sample can comprise a bodily fluid, a wound swab or sample, a rectal swab or sample, another type of biological sample, a culture derived therefrom, or a combination thereof. The bodily fluid can comprise urine, blood, sputum, saliva, breast milk, spinal fluid, semen, vaginal secretions, synovial fluid, pleural fluid, peritoneal fluid, pericardial fluid, amniotic fluid, cultures of bodily fluid that have tested positive for infectious agent growth, or a combination thereof. The infectious agent can comprise bacteria, fungus, mold, or a combination thereof.

DETAILED DESCRIPTION

Variations of the devices, systems, and methods described herein are best understood from the detailed description when read in conjunction with the accompanying drawings. It is emphasized that, according to common practice, the various features of the drawings may not be to scale. On the contrary, the dimensions of the various features may be arbitrarily expanded or reduced for clarity and not all features may be visible or labeled in every drawing. The drawings are taken for illustrative purposes only and are not intended to define or limit the scope of the claims to that which is shown.

Figure 1A:
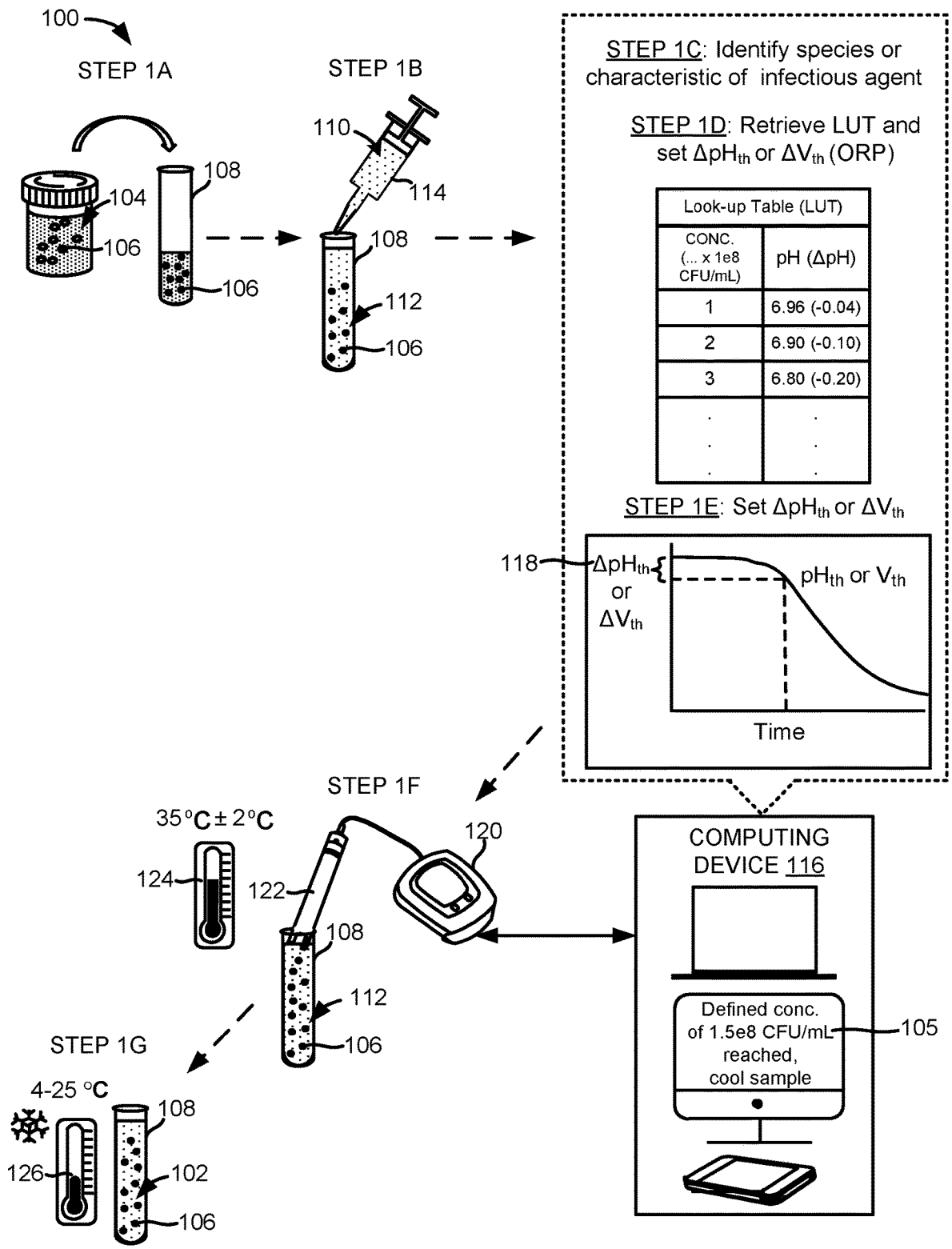
FIG. 1A illustrates certain steps of an example method for preparing an output sample for downstream testing.
Figure 1B:
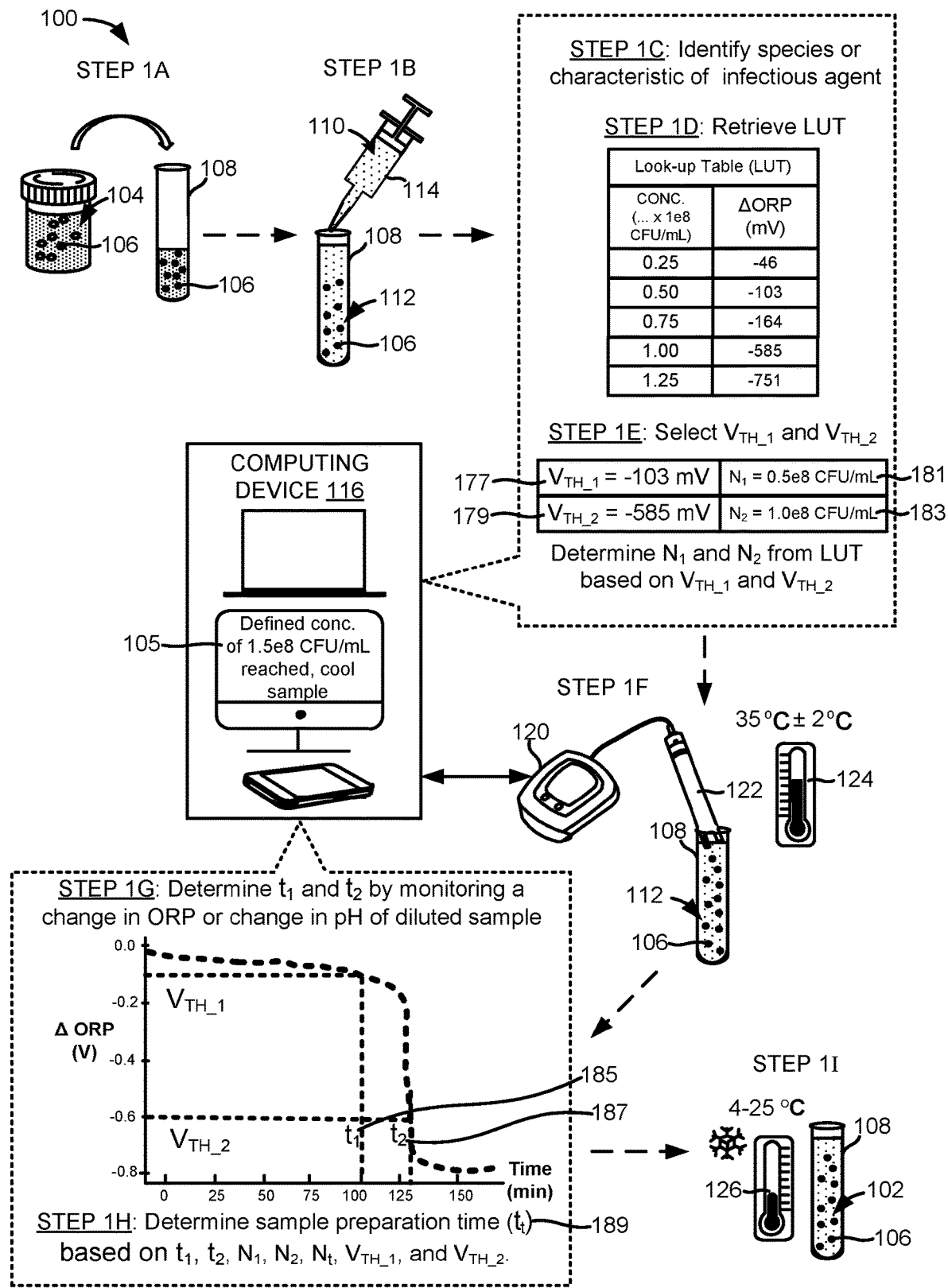
FIG. 1B illustrates certain steps of another example method for preparing an output sample for downstream testing.

FIGS. 1A and 1B illustrate different embodiments of a method 100 for preparing an output sample 102 from a source sample 104 comprising an infectious agent 106. More specifically, the method 100 can provide an output sample 102 comprising a defined concentration 105 of the infectious agent 106 desired by a laboratory technician, clinician, or other operator or user of devices and systems disclosed herein.

The source sample 104 can comprise at least one of a biological sample, a bodily fluid, a wound swab or sample, a rectal swab or sample, and an infectious agent culture derived from the biological sample, the bodily fluid, the wound swab or sample, or the rectal swab or sample. The bodily fluid can comprise urine, blood, serum, plasma, saliva, sputum, semen, breast milk, joint fluid, spinal fluid such as cerebrospinal fluid, wound material, mucus, fluid accompanying stool, re-suspended rectal or wound swabs, vaginal secretions, synovial fluid, pleural fluid, peritoneal fluid, pericardial fluid, amniotic fluid, cultures of bodily fluid or samples that have tested positive for an infectious agent or infectious agent growth such as blood culture that has tested positive for an infectious agent or infectious agent growth (i.e., positive blood culture), or a combination thereof.

The output sample 102 comprising the defined concentration 105 of the infectious agent 106 can be utilized as an inoculum for a downstream test such as a downstream anti-infective or antibiotic susceptibility test (AST) for determining the susceptibility of the infectious agent 106 to one or more anti-infectives or antibiotics.

The infectious agents 106 that can be assayed using the methods or systems disclosed herein can be any metabolizing single- or multi-cellular organism including bacteria and fungi. In certain embodiments, the infectious agent 106 can be bacteria selected from the genera *Acinetobacter, Acetobacter, Actinomyces, Aerococcus, Aeromonas, Agrobacterium, Anaplasma, Azorhizobium, Azotobacter, Bacillus, Bacteroides, Bartonella, Bordetella, Borrelia, Brucella, Burkholderia, Calymmatobacterium, Campylobacter, Chlamydia, Chlamydophila, Citrobacter, Clostridium, Corynebacterium, Coxiella, Ehrlichia, Enterobacter, Enterococcus, Escherichia, Francisella, Fusobacterium, Gardnerella, Haemophilus, Helicobacter, Klebsiella, Lactobacillus, Legionella, Listeria, Methanobacterium, Microbacterium, Micrococcus, Morganella, Moraxella, Mycobacterium, Mycoplasma, Neisseria, Pandoraea, Pasteurella, Peptostreptococcus, Porphyromonas, Prevotella, Proteus, Providencia, Pseudomonas, Ralstonia, Raoultella, Rhizobium, Rickettsia, Rochalimaea, Rothia, Salmonella, Serratia, Shewanella, Shigella, Spirillum, Staphylococcus, Strenotrophomonas, Streptococcus, Streptomyces, Treponema, Vibrio, Wolbachia, Yersinia*, or a combination thereof. In other embodiments, the infectious agent 106 can be one or more fungi selected from the genera *Candida* or *Cryptococcus* or mold.

Other specific bacteria that can be quantified using the methods and systems disclosed herein can comprise *Staphylococcus aureus, Staphylococcus lugdunensis*, coagulase-negative *Staphylococcus* species (including but not limited to *Staphylococcus epidermidis, Staphylococcus haemolyticus, Staphylococcus hominis, Staphylococcus capitis*, not differentiated), *Enterococcus faecalis, Enterococcus faecium* (including but not limited to *Enterococcus faecium* and other *Enterococcus* spp., not differentiated, excluding *Enterococcus faecalis*), *Streptococcus pneumoniae, Streptococcus pyogenes, Streptococcus agalactiae, Streptococcus* spp., (including but not limited to *Streptococcus mitis, Streptococcus pyogenes, Streptococcus gallolyticus, Streptococcus agalactiae, Streptococcus pneumoniae*, not differentiated), *Pseudomonas aeruginosa, Acinetobacter baumannii, Klebsiella* spp. (including but not limited to *Klebsiella pneumoniae, Klebsiella oxytoca*, not differentiated), *Escherichia coli, Enterobacter* spp. (including but not limited to *Enterobacter cloacae, Enterobacter aerogenes*, not differentiated), *Proteus* spp. (including but not limited to *Proteus mirabilis, Proteus vulgaris*, not differentiated), *Citrobacter* spp. (including but not limited to *Citrobacter freundii, Citrobacter koseri*, not differentiated), *Serratia marcescens, Candida albicans, Candida glabrata*, and *Candida tropicalis*.

Other more specific bacteria that can be quantified can comprise *Acinetobacter baumannii, Actinobacillus* spp., *Actinomycetes, Actinomyces* spp. (including but not limited to *Actinomyces israelii* and *Actinomyces naeslundii*), *Aeromonas* spp. (including but not limited to *Aeromonas hydrophila, Aeromonas veronii biovar sobria* (*Aeromonas sobria*), and *Aeromonas caviae*), *Anaplasma phagocytophilum, Alcaligenes xylosoxidans, Actinobacillus actinomycetemcomitans, Bacillus* spp. (including but not limited to *Bacillus anthracis, Bacillus cereus, Bacillus subtilis, Bacillus thuringiensis*, and *Bacillus stearothermophilus*), *Bacteroides* spp. (including but not limited to *Bacteroides fragilis*), *Bartonella* spp. (including but not limited to *Bartonella bacilliformis* and *Bartonella henselae*), *Bifidobacterium* spp., *Bordetella* spp. (including but not limited to *Bordetella pertussis, Bordetella parapertussis*, and *Bordetella bronchiseptica*), *Borrelia* spp. (including but not limited to *Borrelia recurrentis*, and *Borrelia burgdorferi*), *Brucella* spp. (including but not limited to *Brucella abortus, Brucella canis, Brucella melintensis* and *Brucella suis*), *Burkholderia* spp. (including but not limited to *Burkholderia pseudomallei* and *Burkholderia cepacia*), *Campylobacter* spp. (including but not limited to *Campylobacter jejuni, Campylobacter coli, Campylobacter lari* and *Campylobacter fetus*), *Capnocytophaga* spp., *Cardiobacterium hominis, Chlamydia trachomatis, Chlamydophila pneumoniae, Chlamydophila psittaci, Citrobacter* spp., *Coxiella burnetii, Corynebacterium* spp. (including but not limited to, *Corynebacterium diphtheriae, Corynebacterium jeikeum* and *Corynebacterium*), *Clostridium* spp. (including but not limited to *Clostridium perfringens, Clostridium difficile, Clostridium botulinum* and *Clostridium tetani*), *Eikenella corrodens, Enterobacter* spp. (including but not limited to *Enterobacter aerogenes, Enterobacter agglomerans, Enterobacter cloacae* and *Escherichia coli*, including opportunistic *Escherichia coli*, including but not limited to enterotoxigenic *E. coli*, enteroinvasive *E. coli*, enteropathogenic *E. coli*, enterohemorrhagic *E. coli*, enteroaggregative *E. coli* and uropathogenic *E. coli*), *Enterococcus* spp. (including but not limited to *Enterococcus faecalis* and *Enterococcus faecium*), *Ehrlichia* spp. (including but not limited to *Ehrlichia chafeensia* and *Ehrlichia canis*), *Erysipelothrix rhusiopathiae, Eubacterium* spp., *Francisella tularensis, Fusobacterium nucleatum, Gardnerella vaginalis, Gemella morbillorum, Haemophilus* spp. (including but not limited to *Haemophilus influenzae, Haemophilus ducreyi, Haemophilus aegyptius, Haemophilus parainfluenzae, Haemophilus haemolyticus* and *Haemophilus parahaemolyticus*), *Helicobacter* spp. (including but not limited to *Helicobacter pylori, Helicobacter cinaedi* and

*Helicobacter fennelliae*), *Kingella kingii*, *Klebsiella* spp. (including but not limited to *Klebsiella pneumoniae*, *Klebsiella granulomatis* and *Klebsiella oxytoca*), *Lactobacillus* spp., *Listeria monocytogenes*, *Leptospira interrogans*, *Legionella pneumophila*, *Leptospira interrogans*, *Peptostreptococcus* spp., *Moraxella catarrhalis*, *Morganella* spp., *Mobiluncus* spp., *Micrococcus* spp., *Mycobacterium* spp. (including but not limited to *Mycobacterium leprae*, *Mycobacterium tuberculosis*, *Mycobacterium intracellulare*, *Mycobacterium avium*, *Mycobacterium bovis*, and *Mycobacterium marinum*), *Mycoplasm* spp. (including but not limited to *Mycoplasma pneumoniae*, *Mycoplasma hominis*, and *Mycoplasma genitalium*), *Nocardia* spp. (including but not limited to *Nocardia asteroides*, *Nocardia cyriacigeorgica* and *Nocardia brasiliensis*), *Neisseria* spp. (including but not limited to *Neisseria gonorrhoeae* and *Neisseria meningitidis*), *Pasteurella multocida*, *Plesiomonas shigelloides*, *Prevotella* spp., *Porphyromonas* spp., *Prevotella melaninogenica*, *Proteus* spp. (including but not limited to *Proteus vulgaris* and *Proteus mirabilis*), *Providencia* spp. (including but not limited to *Providencia alcalifaciens*, *Providencia rettgeri* and *Providencia stuartii*), *Pseudomonas aeruginosa*, *Propionibacterium acnes*, *Rhodococcus equi*, *Rickettsia* spp. (including but not limited to *Rickettsia rickettsii*, *Rickettsia akari* and *Rickettsia prowazekii*, *Orientia tsutsugamushi* (formerly: *Rickettsia tsutsugamushi*) and *Rickettsia typhi*), *Rhodococcus* spp., *Stenotrophomonas maltophilia*, *Salmonella* spp. (including but not limited to *Salmonella enterica*, *Salmonella typhi*, *Salmonella paratyphi*, *Salmonella enteritidis*, *Salmonella cholerasuis* and *Salmonella typhimurium*), *Serratia* spp. (including but not limited to *Serratia marcesans* and *Serratia liquifaciens*), *Shigella* spp. (including but not limited to *Shigella dysenteriae*, *Shigella flexneri*, *Shigella boydii* and *Shigella sonnei*), *Staphylococcus* spp. (including but not limited to *Staphylococcus aureus*, *Staphylococcus epidermidis*, *Staphylococcus hemolyticus*, *Staphylococcus saprophyticus*), *Streptococcus* spp. (including but not limited to *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae*, *Streptococcus mutans*, *Streptococcus pyogenes*, Group A Streptococci, *Streptococcus pyogenes*, Group B Streptococci, *Streptococcus agalactiae*, Group C Streptococci, *Streptococcus anginosus*, *Streptococcus equismilis*, Group D Streptococci, *Streptococcus bovis*, Group F Streptococci, *Streptococcus anginosus*, and Group G Streptococci), *Spirillum minus*, *Streptobacillus moniliformi*, *Treponema* spp. (including but not limited to *Treponema carateum*, *Treponema petenue*, *Treponema pallidum* and *Treponema endemicum*, *Tropheryma whippelii*, *Ureaplasma urealyticum*, *Veillonella* spp., *Vibrio* spp. (including but not limited to *Vibrio cholerae*, *Vibrio parahemolyticus*, *Vibrio vulnificus*, *Vibrio parahaemolyticus*, *Vibrio vulnificus*, *Vibrio alginolyticus*, *Vibrio mimicus*, *Vibrio hollisae*, *Vibrio fluvialis*, *Vibrio metchnikovii*, *Vibrio damsela* and *Vibrio furnisii*), *Yersinia* spp. (including but not limited to *Yersinia enterocolitica*, *Yersinia pestis*, and *Yersinia pseudotuberculosis*) and *Xanthomonas maltophilia* among others.

Furthermore, other infectious agents 106 that can be assayed using the methods and systems disclosed herein can comprise fungi or mold including, but not limited to, *Candida* spp. (including but not limited to *Candida albicans*, *Candida glabrata*, *Candida tropicalis*, *Candida parapsilosis*, and *Candida krusei*), *Aspergillus* spp. (including but not limited to *Aspergillus fumigatous*, *Aspergillus flavus*, *Aspergillus clavatus*), *Cryptococcous* spp. (including but not limited to *Cryptococcus neoformans*, *Cryptococcus gattii*, *Cryptococcus laurentii*, and *Cryptococcus albidus*), *Fusarium* spp. (including but not limited to *Fusarium oxysporum*, *Fusarium solani*, *Fusarium verticillioides*, and *Fusarium proliferatum*), *Rhizopus oryzae*, *Penicillium marneffei*, *Coccidiodes immitis*, and *Blastomyces dermatitidis*.

FIG. 1A illustrates that the method 100 can comprise introducing aliquots of the source sample 104 into reaction vessels 108 in step 1A. The reaction vessels 108 can refer to one or more test tubes, reaction tubes, wells of a high throughput assay plate or well plate such as a 96-well plate, a 192-well plate, or a 384-well plate, culture plates or dishes, microfluidic conduits, or other suitable containers for housing biological samples.

In additional embodiments not shown in FIGS. 1A and 1B, a stimulus solution can be added to the source sample 104 before metering out aliquots of the source sample 104 to the reaction vessels 108. The stimulus solution can be a nutrient or growth solution. In these and other embodiments, the source sample 104 can also be filtered before step 1A. This filtering step can involve filtering the source sample 104 using an instance of a filter, a microfluidic filter, or a combination thereof to filter out debris, inorganic material, and larger cellular components including blood cells or epithelial cells from the source sample 104.

One or more fluid delivery conduits 110 can inject, deliver, or otherwise introduce aliquots of the source sample 104 to the reaction vessels 108. The fluid delivery conduits 110 can include tubes, pumps, containers, or microfluidic channels for delivering buffers, reagents, fluid samples including the source sample 104, or a combination thereof to and between devices, apparatus, or containers in the system. For example, as shown in FIGS. 1A and 1B, the fluid delivery conduits 110 can refer to parts of a pump such as a syringe pump. In other embodiments, the fluid delivery conduits 110 can include or refer to at least part of a hydraulic pump, a pneumatic pump, a peristaltic pump, a vacuum pump or a positive pressure pump, a manual or mechanical pump, or a combination thereof. In additional embodiments, the fluid delivery conduits 110 can include or refer to at least part of an injection cartridge, a pipette, a capillary, a dispenser bottle, or a combination thereof. The fluid delivery conduits 110 can also be part of a vacuum system configured to draw fluid to or through channels, tubes, or passageways under vacuum. Moreover, the fluid delivery conduits 110 can include or refer to at least part of a multichannel delivery system or pipette.

The method 100 can comprise diluting the aliquots of the source sample 104 in step 1B. For example, the aliquot of the source sample 104 can be diluted by a dilution factor or ratio to yield a diluted sample 112. The dilution factor can be between about 1:1 to about 1:10. The dilution factor can also be between about 1:10 to about 1:100. In some embodiments, the dilution factor can be between about 1:100 to about $1:10^3$. In other embodiments, the dilution factor can also be between about $1:10^3$ to about $1:10^7$. In further embodiments, the dilution factor can be greater than $1:10^7$.

The aliquot of the source sample 104 can be diluted using a dilutive solution 114. In some embodiments, the dilutive solution 114 can comprise growth media or a growth inducer. In these and other embodiments, the dilutive solution 114 can be a solution containing bacto-tryptone, tryptic soy digest, yeast extract, beef extract, cation-adjusted Mueller Hinton Broth (CAMHB), glucose supplemented Mueller Hinton broth (MHG), starch, acid hydrolysate of casein, calcium chloride, magnesium chloride, sodium chloride, blood or lysed blood including lysed horse blood (LHB), CAMHB-LHB, glucose or other carbohydrates, or a combination thereof. The growth inducer can comprise a carbon-based inducer, a nitrogen-based inducer, a mineral, a trace element, a biological growth factor, or any combination thereof. For example, the growth inducer can include but is not limited to a carbohydrate such as glucose or starches, ammonia, magnesium, amino acids, casamino acids, vitamins, peptides, blood, or a combination thereof. In one example embodiment, the dilutive solution 114 can comprise tryptone, yeast extract, sodium chloride, starch, water, and glucose.

Although FIGS. 1A and 1B illustrate one aliquot of the source sample 104 being diluted in step 1B, it is contemplated by this disclosure that additional aliquots of the source sample 104 can be diluted to the same dilution ratio or different dilution ratios to yield additional diluted samples (e.g., a second diluted sample, a third diluted sample, a fourth diluted sample, etc.). The additional diluted samples can be used to generate internal controls or redundant samples.

The method 100 can further comprise an optional step of identifying a species or other classification type or characteristic of the infectious agent 106 in the source sample 104 in step 1C. In addition to species, the other classification type can comprise a genus, a family, an order, a class, a phylum, a kingdom, and a domain of the infectious agent 106 in the source sample 104.

In some embodiments, identifying the species or another classification type of the infectious agent 106 can involve receiving such information from a user via an input device (e.g., a keyboard or touchscreen) coupled to a computing device 116. In other embodiments, identifying the species or another classification type of the infectious agent 106 can involve receiving such information from another computing device communicatively coupled to the computing device 116 or retrieving such information from a database. The classification-type (e.g., the species, the genus, the family, etc.) or the characteristic of the infectious agent 106 can be stored in a memory of the computing device 116, a computing cloud, or a remote server accessible to the computing device 116 over a network.

In some embodiments, identifying the species of the infectious agent 106 in the source sample 104 can involve determining the species 106 using a biochemical test (e.g., a test for metabolism or a test for specific enzymes), mass spectrometry, genotyping, phenotypic analysis from culture plates, test kits comprising phages, or a combination thereof. In some embodiments, the characteristic of the infectious agent 106 can be a response of the infectious agent 106 to a Gram stain test. For example, step 1C can comprise performing a Gram stain test and identifying the infectious agent 106 as Gram-positive or Gram-negative bacteria.

In certain embodiments, the species of the infectious agent 106 in the source sample 104 can be identified but the particular strain of the infectious agent 106 can be left unknown. In other embodiments, the classification-type or characteristic (e.g., the species or Gram-type) of the infectious agent 106 in the source sample 104 does not need to be identified prior to proceeding to other steps of the method 100.

The method 100 can further comprise selecting and retrieving a look-up table (LUT) from a database using the computing device 116 or another device in step 1D. The LUT can be selected based on information concerning a classification-type or characteristic of the infectious agent 106 in the source sample 104 or a lack of such information. For example, a species-specific LUT 210 (see FIG. 2) for the bacterial species *Serratia marcescens* (SMa) can be selected and retrieved when the species of the infectious agent 106 in the source sample 104 is identified as SMa. Also, as an example, a universal LUT 212 (see FIG. 2) can be selected and retrieved when the species of the infectious agent 106 in the source sample 104 has not been ascertained or is unknown. As additional examples, LUTs organized by genus, family, order, class, phylum, kingdom, or domain can also be selected and retrieved. Furthermore, LUTs organized by microbial characteristics, such as Gram-type, or functional capabilities, such as the ability to hydrolyze certain proteins or molecules, can also be selected or retrieved.

The LUTs can be stored as part of a database software program in a memory of the computing device 116. In other embodiments, the LUTs can be stored as part of a database software program in a computing cloud or a remote server accessible to the computing device 116 over a network. The computing device 116 or one or more processors therein can search through hundreds or thousands of stored LUTs and select an appropriate LUT based on information concerning a classification-type (e.g., a species) or characteristic of the infectious agent 106 in the source sample 104.

As will be discussed in more detail in the following sections, the species-specific LUT 210, the universal LUT 212, and other LUTs organized by classification or characteristic can be generated from multiple strain-specific LUTs 204 (see FIG. 2) representing data measured from multiple reference samples 208 (see FIG. 2) monitored over time. When the LUT is a species-specific LUT 210, each of the multiple reference samples 208 can comprise a reference infectious agent 214 (see FIG. 2) of the same species as the infectious agent 106 in the source sample 104. When the LUT is a universal LUT 212 or another type of inter-species LUT, at least one of the multiple reference samples 208 can comprise a reference infectious agent 214 of a different species from the infectious agent 106 in the source sample 104.

The method 100 can further comprise using the computing device 116 or another device communicatively coupled to the computing device 116 to set a threshold amount 118 in step 1E. The threshold amount 118 can represent a target amount by which a solution characteristic of the diluted sample 112 is required to change in order for the concentration of the infectious agent 106 in the diluted sample 112 to reach the defined concentration 105. The threshold amount 118 can also represent a limit or maximum amount by which a solution characteristic of the diluted sample 112 is permitted to change (e.g., ΔpH of approximately −0.20) before the concentration of the infectious agent 106 in the diluted sample 112 exceeds the defined concentration 105.

In some embodiments, the threshold amount 118 can be a threshold range (e.g., ΔpH of between approximately −0.15 and −0.25).

The threshold amount 118 can be set using the computing device 116 (or another device such as a parameter analyzer 120) communicatively coupled to one or more sensors 122 used to monitor the solution characteristic of the diluted sample 112. The threshold amount 118 can be set based on the defined concentration 105, concentration data obtained from the retrieved LUT (e.g., the species-specific LUT 210 or the universal LUT 212), and solution characteristic data obtained from the retrieved LUT (e.g., the species-specific LUT 210 or the universal LUT 212). For example, the defined concentration 105 of the output sample 102 can be set at $3 \times 10^8$ colony-forming units per milliliter (CFU/mL) or 3e8 CFU/mL. Also, for example, the defined concentration 105 of the output sample 102 can be set at $5 \times 10^5$ CFU/mL or 5e5 CFU/mL. Once the computing device 116 (or processors therein) has selected and retrieved an appropriate LUT based on a classification or characteristic of the infectious agent 106 in the source sample 104, the computing device 116 (or processors therein) can then set a threshold amount 118 of ΔpH −0.20 based on concentration and solution characteristic data obtained from the LUT.

The method 100 can further comprise exposing the sensor 122 to the diluted sample 112 or introducing the diluted sample 112 to the sensor 122 such that at least part of the sensor 122 is in fluid communication with the diluted sample 112 in step 1F. The part of the sensor 122 in fluid communication with the diluted sample 112 can comprise a functionalization (or pH-active) layer (see FIGS. 5A, 5B, 7A, and 7B) or a redox-active layer (see FIGS. 6A, 6B, 7A, and 7B) of the sensor 122.

The sensor 122 can be configured to respond to a change in a solution characteristic of the diluted sample 112. In some embodiments, the sensor 122 can be a pH sensor configured to respond to a change in the pH of the diluted sample 112. In other embodiments, the sensor 122 can be an oxidation reduction potential (ORP) sensor configured to respond to a change in the ORP of the diluted sample 112. In additional embodiments, the sensor 122 can be a combined pH and ORP sensor configured to respond to changes in the pH and ORP of the diluted sample 112.

Step 1F can also comprise incubating the diluted sample 112 at an incubation temperature 124 for a period of time. The diluted sample 112 can be incubated while the sensor 122 is exposed to the diluted sample 112. The diluted sample 112 can be incubated in the same reaction vessel 108 or transferred to a different reaction vessel 108 or container.

The incubation temperature 124 can be between approximately 30° C. and 40° C. In some embodiments, the incubation temperature 124 can be between approximately 33° C. and 37° C. (or about 35° C.±2° C.). The diluted sample 112 can be incubated at the incubation temperature 124 for as long as needed for the concentration of the infectious agent 106 within the diluted sample 112 to reach the defined concentration 105. In some embodiments, the incubation period can be between approximately 15 minutes and 60 minutes. In other embodiments, the incubation period can be between approximately 60 minutes and 120 minutes. In additional embodiments, the incubation period can be less than 15 minutes or greater than 120 minutes.

In the example embodiments shown in FIGS. 1A and 1B, exposing the sensor 122 to the diluted sample 112 can involve directly immersing at least part of a handheld or probe instance of the sensor 122 into the diluted sample. In this embodiment, the handheld or probe instance of the sensor 122 can be a handheld pH sensor or a handheld ORP sensor coupled to a standalone parameter analyzer 120, such as a voltmeter or multimeter.

In another example embodiment contemplated by this disclosure, introducing the diluted sample 112 to the sensor 122 can involve injecting, delivering, or otherwise introducing the diluted sample to a well or container comprising the sensor 122 fabricated on a substrate. In yet another example embodiment shown in FIG. 4A, introducing the diluted sample 112 to the sensor 122 can involve placing or positioning a reaction vessel 404 (see FIG. 4A) comprising the diluted sample 112 into a sample preparation apparatus 402 (see FIG. 4A) comprising built-in sensors 122 having contacts or electrodes able to access or be in fluid communication with the diluted sample 112. The sensor 122 will be discussed in more detail in the following sections.

Step 1F can further comprise monitoring a change in the solution characteristic of the diluted sample 112 using a parameter analyzer 120 coupled to the sensor 122 or a computing device 116 coupled to the parameter analyzer 120 or the sensor 122. The solution characteristic of the diluted sample 112 can be monitored in the absence of any exogenous reporter molecules added to the diluted sample 112.

Although FIGS. 1A and 1B show the parameter analyzer 120 as a separate standalone device from the computing device 116, it is contemplated by this disclosure and it should be understood by one of ordinary skill in the art that the parameter analyzer 120 and the computing device 116 can be integrated into one device. As illustrated in FIGS. 1A and 1B, the computing device 116 can be a mobile device, a handheld device, a tablet device, a laptop or desktop computer. In some embodiments, the parameter analyzer 120 can wirelessly communicate a signal or result to the computing device 116.

The solution characteristic of the diluted sample 112 can change as the amount of ions or the amount of electro-active redox species in solution change due to the energy use, oxygen uptake or release, growth, or metabolism of the infectious agent 106 in the diluted sample 112. For example, the amount of electro-active redox species in the diluted sample 112 can change as a result of cellular activity (e.g., microbial aerobic or anaerobic respiration) undertaken by the infectious agents 106 in the diluted sample 112. Also, as an example, the amount of $H^+$ ions in the diluted sample 112 can change as a result of cellular activity undertaken by the infectious agents 106 in the diluted sample 112.

As a more specific example, the amount of electron donors from Table 1 below (e.g., the amount of energy carriers such as nicotinamide adenine dinucleotide (NADH) and flavin adenine dinucleotide ($FADH_2$)) in the diluted sample 112 can change due to the growth of the infectious agent 106 in the diluted sample 112. Also, as another more specific example, the amount of oxygen depleted in the diluted sample 112 due to aerobic respiration can change due to the growth of the infectious agent 106 in the diluted sample 112.

TABLE 1

Below is a "redox tower" visualizing potential electron donors and acceptors which can be utilized by infectious agents during the course of metabolism. An electron donor will have a greater negative potential than the electron acceptor. In aerobic respiration for example, $O_2$ can serve as a terminal electron acceptor whereas in anaerobic respiration, the terminal electron acceptor can comprise $NO_3^-$, $Fe^{3+}$, $Mn^{4+}$, $SO_4^{2-}$, or $CO_2$.

| Electron Donor and Acceptor Pairs | Measured Standard Reduction Potential $E'_0$ (mV) | Standard Reduction Potential $E'_0$ (mV) range |
|---|---|---|
| Glucose ⇌ 2 Pyruvate + 2e⁻ | −720 | −700 |
|  |  | −600 |
| Glucose ⇌ 6 $CO_2$ + 24e⁻ | −500 | −500 |
| $H_2$ ⇌ 2$H^+$ + 2e⁻ | −420 | −400 |
| NADH ⇌ $NAD^+$ + 2e⁻ | −320 | −300 |
| 2 GSH ⇌ GSSG + 2e⁻ | −240 | −200 |
| $H_2S$ ⇌ $SO_4^{2-}$ + 8e⁻ | −220 |  |
| $FADH_2$ ⇌ FAD + 2$H^+$ + 2e⁻ | −220 |  |
| Lactate ⇌ Pyruvate + 2e⁻ | −190 | −100 |
| Succinate ⇌ Fumarate + 2e⁻ | 33 | 0 |
| Cyt b (red) ⇌ Cyt b (ox) + e⁻ | 80 |  |
| Ubiquinol ⇌ Ubiquinone + 2e⁻ | 110 | 100 |
| Cyt c (red) ⇌ Cyt c (ox) + e⁻ | 250 | 200 |
| Cyt a (red) ⇌ Cyt a (ox) + e⁻ | 290 |  |
|  |  | 300 |
| $NO_2^-$ + $H_2O$ ⇌ $NO_3^-$ + 2e⁻ | 420 | 400 |
| $NH_4^+$ + $H_2O$ ⇌ $NO_2^-$ + 6e⁻ | 440 |  |
| $Mn^{2+}$ + $H_2O$ ⇌ $MnO_2$ + 2e⁻ | 460 |  |
|  |  | 500 |
|  |  | 600 |
| ½ $N_2$ + 3$H_2O$ ⇌ $NO_3^-$ + 5e⁻ | 740 | 700 |
| $Fe^{2+}$ ⇌ $Fe^{3+}$ + 1e⁻ | 770 |  |
| $H_2O$ ⇌ ½ $O_2$ + 2$H^+$ + 2e⁻ | 820 | 800 |
|  |  | 700 |

When the solution characteristic monitored is pH, the threshold amount 118 can be between approximately ΔpH 0.01 and ΔpH 3.0. As a more specific example, the threshold amount 118 can be set at approximately ΔpH 0.20 (i.e., a pH threshold level ($pH_{th}$) of pH 6.8 can be set when a starting pH is normalized to pH 7.0). When the solution characteristic monitored is ORP, the threshold amount 118 can be between approximately Δ100 mV and Δ700 mV. As a more specific example, the threshold amount 118 can be set at approximately Δ100 mV (i.e., an ORP threshold level ($V_{th}$) of −100 mV can be set when a starting ORP is normalized to 0 mV).

The method 100 can further comprise cooling the diluted sample 112 to a cooling temperature 126 when the solution characteristic of the diluted sample 112 changes by the threshold amount 118 in step 1G. The diluted sample 112 can be cooled when the concentration of the infectious agent 106 within the diluted sample 112 reaches the defined concentration 105 (i.e., when the threshold amount 118 is reached). Once the concentration of the infectious agent 106 within the diluted sample 112 reaches the defined concentration 105, the diluted sample 112 can be considered or referred to as the output sample 102.

The cooling temperature 126 can be between approximately 4° C. and 25° C. In some embodiments, the cooling temperature 126 can be between approximately 4° C. and 15° C. In other embodiments, the cooling temperature 126 can be below 4° C. and above 25° C.

In one embodiment, the computing device 116 or the parameter analyzer 120 can alert a user that the solution characteristic of the diluted sample 112 has changed by the threshold amount 118. For example, the computing device 116 or the parameter analyzer 120 can generate an audible alert, a visual or graphic alert, a haptic or motion alert, or a combination thereof when the solution characteristic of the diluted sample 112 has changed by the threshold amount 118. As a more specific example, the computing device 116 or the parameter analyzer 120 can generate a message informing a user that the solution characteristic of the diluted sample 112 has changed by the threshold amount 118.

The diluted sample 112 can be cooled to the cooling temperature 126 by being placed in an ice bath. The diluted sample 112 can also be cooled to the cooling temperature 126 by being placed in a refrigerator or freezer, a cold compartment, a cooling device, or a combination thereof. When the method 100 is implemented using an integrated system such as the system 400 shown in FIG. 4A, the diluted sample 112 can be cooled by a cooling component integrated within the sample preparation apparatus 402 (see FIG. 4A).

The method 100 can further comprise diluting the output sample 102 by another dilution factor to yield a further diluted sample. The further diluted sample can comprise an infectious agent concentration required for a downstream test such as a downstream AST assay. In this case, the further diluted sample can serve as the input sample for the downstream test. The diluent in the further diluted sample can be of any temperature including a diluent having a temperature between approximately 4° C. and 25° C. and, thus, can act as a coolant to cool the further diluted sample.

FIG. 1B illustrates that another embodiment of the method 100 can comprise introducing aliquots of the source sample 104 into reaction vessels 108 in step 1A. The reaction vessels 108 can refer to one or more test tubes, reaction tubes, wells of a high throughput assay plate or well plate such as a 96-well plate, a 192-well plate, or a 384-well plate, culture plates or dishes, microfluidic conduits, or other suitable containers for housing biological samples.

In additional embodiments not shown in FIGS. 1A and 1B, a stimulus solution can be added to the source sample 104 before metering out aliquots of the source sample 104 to the reaction vessels 108. The stimulus solution can be a nutrient or growth solution. In these and other embodiments, the source sample 104 can also be filtered before step 1A. This filtering step can involve filtering the source sample 104 using an instance of a filter, a microfluidic filter, or a combination thereof to filter out debris, inorganic material, and larger cellular components including blood cells or epithelial cells from the source sample 104.

One or more fluid delivery conduits 110 can inject, deliver, or otherwise introduce aliquots of the source sample 104 to the reaction vessels 108. The fluid delivery conduits 110 can include tubes, pumps, containers, or microfluidic channels for delivering buffers, reagents, fluid samples including the source sample 104, or a combination thereof to and between devices, apparatus, or containers in the system. For example, as shown in FIGS. 1A and 1B, the fluid delivery conduits 110 can refer to parts of a pump such as a syringe pump. In other embodiments, the fluid delivery conduits 110 can include or refer to at least part of a hydraulic pump, a pneumatic pump, a peristaltic pump, a vacuum pump or a positive pressure pump, a manual or mechanical pump, or a combination thereof. In additional embodiments, the fluid delivery conduits 110 can include or refer to at least part of an injection cartridge, a pipette, a capillary, a dispenser bottle, or a combination thereof. The fluid delivery conduits 110 can also be part of a vacuum system configured to draw fluid to or through channels, tubes, or passageways under vacuum. Moreover, the fluid delivery conduits 110 can include or refer to at least part of a multichannel delivery system or pipette.

The method 100 can comprise diluting the aliquots of the source sample 104 in step 1B. For example, the aliquot of the source sample 104 can be diluted by a dilution factor or ratio to yield a diluted sample 112. The dilution factor can be between about 1:1 to about 1:10. The dilution factor can also be between about 1:10 to about 1:100. In some embodiments, the dilution factor can be between about 1:100 to about $1:10^3$. In other embodiments, the dilution factor can also be between about $1:10^3$ to about $1:10^7$. In further embodiments, the dilution factor can be greater than $1:10^7$.

The aliquot of the source sample 104 can be diluted using a dilutive solution 114. In some embodiments, the dilutive solution 114 can comprise growth media or a growth inducer. In these and other embodiments, the dilutive solution 114 can be a solution containing bacto-tryptone, tryptic soy digest, yeast extract, beef extract, cation-adjusted Mueller Hinton Broth (CAMHB), glucose supplemented Mueller Hinton broth (MHG), starch, acid hydrolysate of casein, calcium chloride, magnesium chloride, sodium chloride, blood or lysed blood including lysed horse blood (LHB), CAMHB-LHB, glucose or other carbohydrates, or a combination thereof. The growth inducer can comprise a carbon-based inducer, a nitrogen-based inducer, a mineral, a trace element, a biological growth factor, or any combination thereof. For example, the growth inducer can include but is not limited to a carbohydrate such as glucose or starches, ammonia, magnesium, amino acids, casamino acids, vitamins, peptides, blood, or a combination thereof. In one example embodiment, the dilutive solution 114 can comprise tryptone, yeast extract, sodium chloride, starch, water, and glucose.

Although FIGS. 1A and 1B illustrate one aliquot of the source sample 104 being diluted in step 1B, it is contemplated by this disclosure that additional aliquots of the source sample 104 can be diluted to the same dilution ratio or different dilution ratios to yield additional diluted samples (e.g., a second diluted sample, a third diluted sample, a fourth diluted sample, etc.). The additional diluted samples can be used to generate internal controls or redundant samples.

The method 100 can further comprise an optional step of identifying a species or other classification type or characteristic of the infectious agent 106 in the source sample 104 in step 1C. In addition to species, the other classification type can comprise a genus, a family, an order, a class, a phylum, a kingdom, and a domain of the infectious agent 106 in the source sample 104.

In some embodiments, identifying the species or another classification type of the infectious agent 106 can involve receiving such information from a user via an input device (e.g., a keyboard or touchscreen) coupled to a computing device 116. In other embodiments, identifying the species or another classification type of the infectious agent 106 can involve receiving such information from another computing device communicatively coupled to the computing device 116 or retrieving such information from a database. The classification-type (e.g., the species, the genus, the family, etc.) or the characteristic of the infectious agent 106 can be stored in a memory of the computing device 116, a computing cloud, or a remote server accessible to the computing device 116 over a network.

In some embodiments, identifying the species of the infectious agent 106 in the source sample 104 can involve determining the species 106 using a biochemical test (e.g., a test for metabolism or a test for specific enzymes), mass spectrometry, genotyping, phenotypic analysis from culture plates, test kits comprising phages, or a combination thereof. In some embodiments, the characteristic of the infectious agent 106 can be a response of the infectious agent 106 to a Gram stain test. For example, step 1C can comprise performing a Gram stain test and identifying the infectious agent 106 as Gram-positive or Gram-negative bacteria.

In certain embodiments, the species of the infectious agent 106 in the source sample 104 can be identified but the particular strain of the infectious agent 106 can be left unknown. In other embodiments, the classification-type or characteristic (e.g., the species or Gram-type) of the infectious agent 106 in the source sample 104 does not need to be identified prior to proceeding to other steps of the method 100.

The method 100 can further comprise selecting and retrieving a look-up table (LUT) from a database using the computing device 116 or another device in step 1D. The LUT can be selected based on information concerning a classification-type or characteristic of the infectious agent 106 in the source sample 104 or a lack of such information. For example, a species-specific LUT 210 (see, e.g., FIG. 3C or 3D) for the bacterial species *Escherichia coli* (ECo) can be selected and retrieved when the species of the infectious agent 106 in the source sample 104 is identified as ECo. Also, as another example, a universal LUT 212 (see, e.g., FIG. 2) can be selected and retrieved when the species of the infectious agent 106 in the source sample 104 has not been ascertained or is unknown. In further embodiments, LUTs organized by genus, family, order, class, phylum, kingdom, or domain can also be selected and retrieved. Furthermore, LUTs organized by microbial characteristics, such as Gram-type, or functional capabilities, such as the ability to hydrolyze certain proteins or molecules, can also be selected or retrieved.

The LUTs can be stored as part of a database software program in a memory of the computing device 116. In other embodiments, the LUTs can be stored as part of a database software program in a computing cloud or a remote server accessible to the computing device 116 over a network. The computing device 116 or one or more processors therein can search through hundreds or thousands of stored LUTs and select an appropriate LUT based on information concerning a classification-type (e.g., a species) or characteristic of the infectious agent 106 in the source sample 104.

As will be discussed in more detail in the following sections, the species-specific LUT 210, the universal LUT 212, and other LUTs organized by classification or characteristic can be generated from multiple strain-specific LUTs 204 (see, e.g., FIGS. 2, 3A, 3C, and 3D) representing data measured from multiple reference samples 208 (see, e.g., FIG. 2) monitored over time. When the LUT is a species-specific LUT 210, each of the multiple reference samples 208 can comprise a reference infectious agent 214 (see FIG. 2) of the same species as the infectious agent 106 in the source sample 104. When the LUT is a universal LUT 212 or another type of inter-species LUT, at least one of the multiple reference samples 208 can comprise a reference infectious agent 214 of a different species from the infectious agent 106 in the source sample 104.

The method 100 can further comprise selecting at least a first threshold amount 177 ($V_{TH\_1}$) and a second threshold amount 179 ($V_{TH\_2}$) from the LUT (e.g., any of the species-specific LUT 210 or the universal LUT 212) in step 1E. The LUT can associate a first concentration 181 ($N_1$) with the first threshold amount 177 (or $V_{TH\_1}$) and associate a second concentration 183 ($N_2$) with the second threshold amount 179 (or $V_{TH\_2}$). The first threshold amount 177 ($V_{TH\_1}$), the first concentration 181 ($N_1$), the second threshold amount 179 ($V_{TH\_2}$), and the second concentration 183 ($N_2$) can be recorded and stored in a memory of the computing device 116 or another device or stored in a database accessible to the computing device 116 or another device.

The first threshold amount 177 (or $V_{TH\_1}$) and the second threshold amount 179 (or $V_{TH\_2}$) can be selected based in part on the defined concentration 105 desired. For example, the first threshold amount 177 (or $V_{TH\_1}$) and the second threshold amount 179 (or $V_{TH\_2}$) can be selected because the first concentration 181 ($N_1$) and the second concentration 183 ($N_2$) precede the defined concentration 105 (i.e., the amount of the defined concentration 105 is greater than the first concentration 181 ($N_1$) and the second concentration 183 ($N_2$)).

As will be discussed in the following sections, the first threshold amount 177 (or $V_{TH\_1}$), the second threshold amount 179 (or $V_{TH\_2}$), the first concentration 181 (or $N_1$), and the second concentration 183 (or $N_2$) can be used along with other parameters (to be discussed in the following sections) to determine an amount of time necessary for the infectious agent 106 within the diluted sample 112 to reach the defined concentration 105.

The method 100 can further comprise exposing the sensor 122 to the diluted sample 112 or introducing the diluted sample 112 to the sensor 122 such that at least part of the sensor 122 is in fluid communication with the diluted sample 112 in step 1F. The part of the sensor 122 in fluid communication with the diluted sample 112 can comprise a redox-active layer (see FIGS. 6A, 6B, 7A, and 7B) or a functionalization (or pH-active) layer (see FIGS. 5A, 5B, 7A, and 7B) of the sensor 122.

The sensor 122 can be configured to respond to a change in a solution characteristic of the diluted sample 112. In some embodiments, the sensor 122 can be an oxidation reduction potential (ORP) sensor configured to respond to a change in the ORP of the diluted sample 112. In other embodiments, the sensor 122 can be a pH sensor configured to respond to a change in the pH of the diluted sample 112. In additional embodiments, the sensor 122 can be a combined pH and ORP sensor configured to respond to changes in the pH and ORP of the diluted sample 112.

Step 1F can also comprise incubating the diluted sample 112 at an incubation temperature 124 for a period of time. The diluted sample 112 can be incubated while the sensor 122 is exposed to the diluted sample 112. The diluted sample 112 can be incubated in the same reaction vessel 108 or transferred to a different reaction vessel 108 or container.

The incubation temperature 124 can be between approximately 30° C. and 40° C. In some embodiments, the incubation temperature 124 can be between approximately 33° C. and 37° C. (or about 35° C.±2° C.). The diluted sample 112 can be incubated at the incubation temperature 124 for as long as needed for the concentration of the infectious agent 106 within the diluted sample 112 to reach the defined concentration 105. In some embodiments, the incubation period can be between approximately 15 minutes and 60 minutes. In other embodiments, the incubation period can be between approximately 60 minutes and 120 minutes. In additional embodiments, the incubation period can be less than 15 minutes or greater than 120 minutes.

In the example embodiments shown in FIGS. 1A and 1B, exposing the sensor 122 to the diluted sample 112 can involve directly immersing at least part of a handheld or probe instance of the sensor 122 into the diluted sample. In this embodiment, the handheld or probe instance of the sensor 122 can be a handheld pH sensor or a handheld ORP sensor coupled to a standalone parameter analyzer 120, such as a voltmeter or multimeter.

In another example embodiment contemplated by this disclosure, introducing the diluted sample 112 to the sensor 122 can involve injecting, delivering, or otherwise introducing the diluted sample to a well or container comprising the sensor 122 fabricated on a substrate. In yet another example embodiment shown in FIG. 4A, introducing the diluted sample 112 to the sensor 122 can involve placing or positioning a reaction vessel 404 (see FIG. 4A) comprising the diluted sample 112 into a sample preparation apparatus 402 (see FIG. 4A) comprising built-in sensors 122 having contacts or electrodes able to access or be in fluid communication with the diluted sample 112. The sensor 122 will be discussed in more detail in the following sections.

Step 1G can comprise monitoring a change in the solution characteristic of the diluted sample 112 using a parameter analyzer 120 coupled to the sensor 122 or a computing device 116 coupled to the parameter analyzer 120 or the sensor 122. The solution characteristic of the diluted sample 112 can be monitored in the absence of any exogenous reporter molecules added to the diluted sample 112.

Although FIGS. 1A and 1B show the parameter analyzer 120 as a separate standalone device from the computing device 116, it is contemplated by this disclosure and it should be understood by one of ordinary skill in the art that the parameter analyzer 120 and the computing device 116 can be integrated into one device. As illustrated in FIGS. 1A and 1B, the computing device 116 can be a mobile device, a handheld device, a tablet device, a laptop or desktop computer. In some embodiments, the parameter analyzer 120 can wirelessly communicate a signal or result to computing device 116.

The solution characteristic of the diluted sample 112 can change as the amount of ions or the amount of electro-active redox species in solution change due to the energy use, oxygen uptake or release, growth, or metabolism of the infectious agent 106 in the diluted sample 112.

Step 1G can further comprise obtaining a first threshold time 185 ($t_1$) corresponding to an amount of time elapsed for the solution characteristic of the diluted sample 112 to change by the first threshold amount 177. In addition, step 1G can also comprise obtaining a second threshold time 187 ($t_2$) corresponding to an amount of time elapsed for the solution characteristic of the diluted sample 112 to change by the second threshold amount 179. The computing device 116, the parameter analyzer 120, or a combination thereof can record and store the first threshold time 185 (or $t_1$) and the second threshold time 187 (or $t_2$) in a memory of the computing device 116 or the parameter analyzer 120 or in a database accessible by the computer device 116, the parameter analyzer 120, or a combination thereof.

The method 100 can further comprise determining a sample preparation time 189 ($t_r$) corresponding to the amount of time necessary for the infectious agent 106 within the diluted sample 112 to reach the defined concentration 105 in step 1H. The sample preparation time 189 ($t_r$) can be determined based on the first threshold amount 177 (or $V_{TH\_1}$), the second threshold amount 179 (or $V_{TH\_2}$), the first concentration 181 (or $N_1$), the second concentration 183 (or $N_2$), defined concentration 105 ($N_r$), the first threshold time 185 (or $t_1$), and the second threshold time 187 (or $t_2$).

For example, in some embodiments, the sample preparation time 189 (or $t_r$) can be calculated using Equation 1 below:

$$t_t = t_2 + \frac{\log\left(\frac{N_t}{N_2}\right)}{\log\left(\frac{N_2}{N_1}\right)} \times (t_2 - t_1) \quad \text{(Equation 1)}$$

As a more specific example, the sample preparation time 189 (or $t_t$) can be calculated using the values in Table 1 below for a defined concentration 105 (or $N_t$) of 1.5e8 CFU/mL.

TABLE 1

Threshold values and times to detection used to calculate sample preparation time ($t_t$)

| | | |
|---|---|---|
| $V_{TH\_1}$ = −103 mV | $N_1$ = 0.5e8 CFU/ml | $t_1$ = 100 mins |
| $V_{TH\_1}$ = −585 mV | $N_2$ = 1.0e8 CFU/ml | $t_2$ = 130.5 mins |

$$t_t = 130.5 \text{ min} + \frac{\log\left(\frac{1.5e^8 \text{ CFU/ml}}{1.0e^8 \text{ CFU/ml}}\right)}{\log\left(\frac{1.0e^8 \text{ CFU/ml}}{0.5e^8 \text{ CFU/ml}}\right)} \times (130.5 \text{ min} - 100 \text{ min})$$

$$t_t = 130.5 \text{ min} + \frac{\log(1.5)}{\log(2.0)} \times (130.5 \text{ min} - 100 \text{ min})$$

$t_t$ = 130.5 min + 0.585 × (30.5 min)
$t_t$ = 148.3 min

As shown above, the sample preparation time 189 can be calculated as 148.3 minutes for a defined concentration 105 (or $N_t$) of 1.5e8 CFU/mL using Equation 1 and the threshold amounts and times-to-detection provided above.

The method 100 can further comprise cooling the diluted sample 112 to a cooling temperature 126 when the calculated sample preparation time (or $N_t$) is reached in step 1I. Once the sample preparation time 189 ($N_t$) is reached, the concentration of the infectious agent 106 within the diluted sample 112 should be close to or substantially equivalent to the defined concentration 105 desired. Also, once the sample preparation time 189 is reached and the diluted sample 112 is cooled, the sample can be considered or referred to as the output sample 102.

The cooling temperature 126 can be between approximately 4° C. and 25° C. In some embodiments, the cooling temperature 126 can be between approximately 4° C. and 15° C. In other embodiments, the cooling temperature 126 can be below 4° C. and above 25° C.

In one embodiment, the computing device 116 or the parameter analyzer 120 can alert a user once the sample preparation time 189 has been reached. For example, the computing device 116 or the parameter analyzer 120 can generate an audible alert, a visual or graphic alert, a haptic or motion alert, or a combination thereof when the sample preparation time 189 has been reached. As a more specific example, the computing device 116 or the parameter analyzer 120 can generate a message informing a user that the sample preparation time 189 has been reached.

The diluted sample 112 can be cooled to the cooling temperature 126 by being placed in an ice bath. The diluted sample 112 can also be cooled to the cooling temperature 126 by being placed in a refrigerator or freezer, a cold compartment, a cooling device, or a combination thereof. When the method 100 is implemented using an integrated system such as the system 400 shown in FIG. 4A, the diluted sample 112 can be cooled by a cooling component integrated within the sample preparation apparatus 402 (see FIG. 4A).

The method 100 can further comprise diluting the output sample 102 by another dilution factor to yield a further diluted sample. The further diluted sample can comprise an infectious agent concentration required for a downstream test such as a downstream AST assay. In this case, the further diluted sample can serve as the input sample for the downstream test. The diluent in the further diluted sample can be of any temperature including a diluent having a temperature between approximately 4° C. and 25° C. and, thus, can act as a coolant to cool the further diluted sample.

The method 100 shown in FIG. 1B can be used when a defined concentration 105 (and its accompanying solution characteristic change) is not included in a previously stored look-up table (i.e., when the amount of the defined concentration 105 desired is not included in any stored LUTs). In addition, the method 100 shown in FIG. 1B can be used when an ORP signal or pH signal monitored changes significantly or fluctuates outside of an acceptable range after an initial period such that any later changes in the solution characteristic of the diluted sample 112 are not reliable for pinpointing a defined concentration 105.

Using the methods 100 and systems described herein, a laboratory or hospital can prepare an output sample 102 of a defined concentration 105 from a source sample 104 within a shortened preparation period. Using the methods 100 and systems described herein, the preparation period can be between approximately 60 minutes and 120 minutes. In other embodiments, the preparation period can be between approximately 1 minute and 60 minutes. In additional embodiments, the preparation period can be between approximately 120 minutes and 240 minutes. In some embodiments, the preparation period can be greater than 240 minutes.

One or more of the aforementioned steps of the methods 100 can be stored as machine-executable instructions or logical commands in a non-transitory machine-readable medium (e.g., a memory or storage unit) of the computing device 116 or another device communicatively or electrically coupled to the computing device 116. Any of the parameter analyzer 120, the computing device 116, or another device coupled to the parameter analyzer 120 or the computing device 116 can comprise one or more processors or controllers configured to execute the aforementioned instructions or logical commands.

The steps depicted in FIGS. 1A and 1B do not require the particular order shown to achieve the desired result. Moreover, certain steps or processes may be omitted or occur in parallel in order to achieve the desired result. In addition, any of the systems or devices disclosed herein can be used in lieu of devices or systems shown in the steps of FIG. 1A or 1B.

Figure 2:
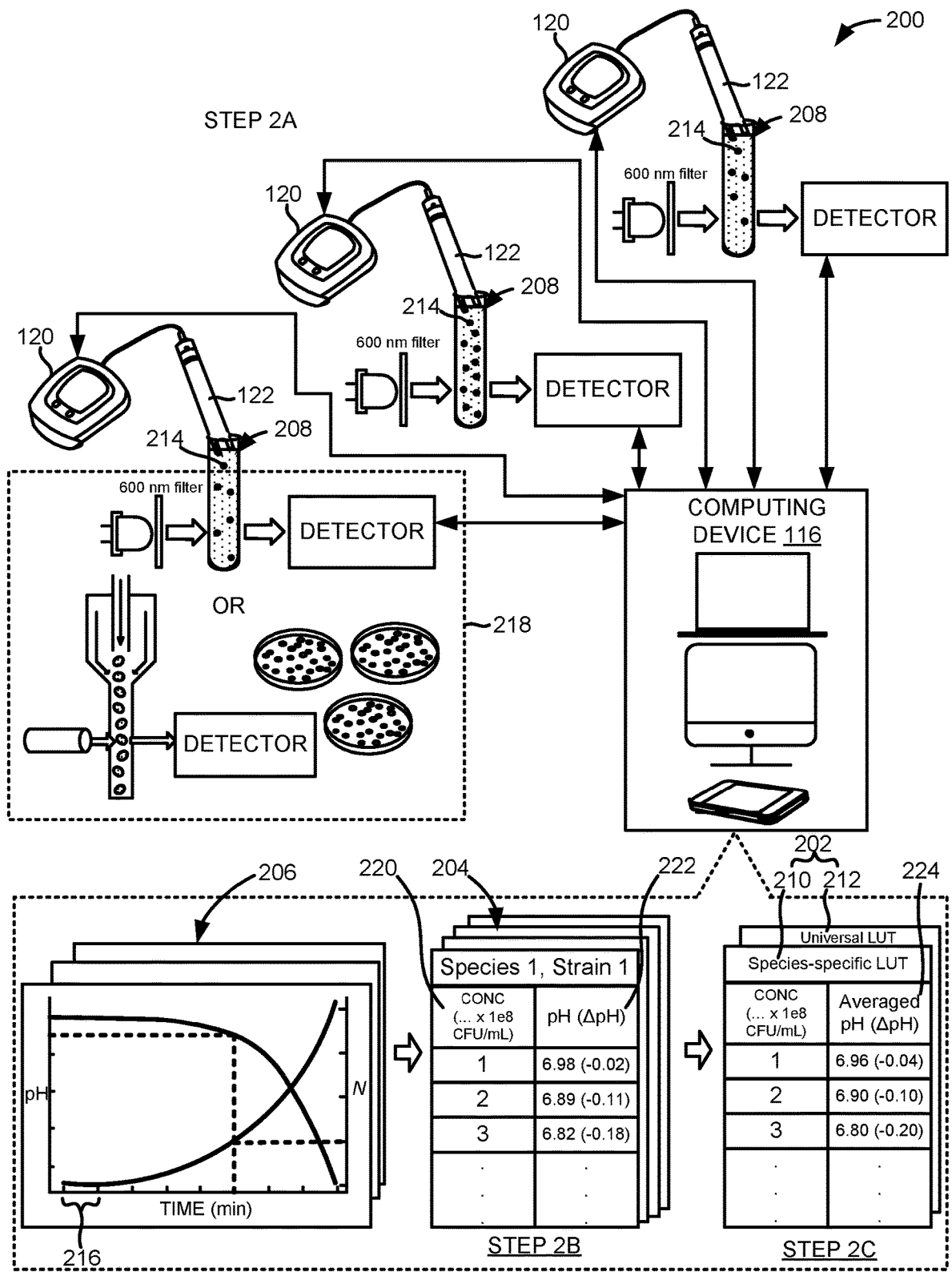
FIG. 2 illustrates additional steps of the example method for preparing an output sample for downstream testing.

FIG. 2 illustrates an example method 200 for generating a composite or averaged look-up table (LUT) 202 from multiple strain-specific LUTs 204. The multiple strain-specific LUTs 204 can represent experimental data 206 obtained from monitoring multiple reference samples 208 over time. The averaged LUT 202 can be any of the species-specific LUT 210, the universal LUT 212, or another LUT organized by classification-type or characteristic. For example, the averaged LUT 202 can also be a Gram-positive LUT or a Gram-negative LUT. Each of the reference samples 208 can comprise a reference infectious agent 214 of a known strain and a known species.

The species-specific LUT 210 can be generated from multiple strain-specific LUTs 204 representing experimental data 206 obtained from monitoring multiple reference samples 208 where each of the references samples 208 comprises a reference infectious agent 214 of the same species as the infectious agent 106 in the source sample 104. For example, a species-specific LUT 210 can be generated for SMa from multiple strain-specific LUTs 204 including LUTs representing the CDC-27 strain of SMa (SMa_CDC-27), the CDC-91 strain of SMa (SMa_CDC-91), the CDC-99 strain of SMa (SMa_CDC-99), the CDC-121 strain of SMa (SMa_CDC-121), the CDC-122 strain of SMa (SMa_CDC-122), the CDC-130 strain of SMa (SMa_CDC-130), or a combination thereof. As another example, a species-specific LUT 210 can also be generated for *Staphylococcus aureus* (SAu) from multiple strain-specific LUTs 204 including LUTs comprising the wildtype strain of SAu (SAu_WT), the CDC-483 strain of SAu (SAu_CDC-483), the CDC-475 strain of SAu (SAu_CDC-475), the ATCC43300 strain of SAu (SAu-ATCC-43300), or a combination thereof.

The universal LUT 212 can be generated from multiple strain-specific LUTs 204 representing experimental data 206 obtained from monitoring multiple reference samples 208 comprising references infectious agents 214 of different species. For example, a universal LUT 212 can be generated from multiple strain-specific LUTs 204 across several species including strain-specific LUTs 204 representing the species SMa, SAu, *Escherichia coli* (ECo), *Enterobacter cloacae* (ECl), *Enterobacter aerogenes* (EAe), *Klebsiella pneumoniae* (KPn), or any combination thereof.

The reference samples 208 can be prepared by re-suspending infectious agent colonies from an infectious agent culture plate into growth media to reach an initial concentration. As a more specific example, the reference samples can be liquid bacterial cultures prepared by inoculating bacterial colonies from a bacterial culture plate into growth media. For example, the initial concentration of reference infectious agents 214 can be approximately $1 \times 10^7$ (or 1e7) CFU/mL.

The method 200 can comprise monitoring changes in the solution characteristic of the reference samples 208 over a period of time in step 2A. The solution characteristics can be monitored by introducing the reference samples 208 to the sensors 122 or otherwise exposing the sensors 122 to the reference samples 208 such that a functionalization layer (see FIGS. 5A, 5B, 7A, and 7B) or a redox-active layer (see FIGS. 6A, 6B, 7A, and 7B) of the sensors 122 is in fluid communication with the reference samples 208. When the sensors 122 are pH sensors, the solution characteristic monitored can be solution pH. When the sensors 122 are ORP sensors, the solution characteristic monitored can be solution ORP. The solution characteristics of the reference samples 208 can be monitored in the absence of any exogenous reporter molecules added to the reference samples 208. The reference samples 208 can also be incubated at an incubation temperature 124 while the solution characteristics of the reference samples 208 are monitored by the sensors 122.

In some embodiments, the sensors 122 can be coupled to parameter analyzers 120 communicatively coupled to the computing device 116 or the sensors 122 can be coupled directly to the computing device 116. The computing device 116 can record and store data concerning a change in the solution characteristic of a reference sample 208 at specific time intervals 216. For example, the computing device 116 can store a change in the pH of a reference sample 208 every 5 minutes, every 10 minutes, or every 15 minutes. In some embodiments, the time intervals 216 can be between approximately 30 seconds and 20 minutes. In other embodiments, the time intervals 216 can be between approximately 1 second and 30 seconds or greater than 20 minutes.

The method 200 can further comprise conducting sample enumeration assays 218 of the references samples 208 over the same period of time. A sample enumeration assay 218 can be a test or measurement conducted in order to determine a concentration of a reference infectious agent 214 in a reference sample 208 at a particular point in time. The concentration of the reference infectious agent 214 in the reference sample 208 can increase over a period of time as the reference samples 208 are incubated and the growth media provides nutrients for the reference infectious agent 214.

In some embodiments, the sample enumeration assay 218 can comprise an optical density (O.D.) measurement, a plate count assay, or a flow cytometry assay. In other embodiments, the sample enumeration assay 218 can be other tests or measurements for determining a concentration of a reference infectious agent 214 in a reference sample 208. For example, the sample enumeration assay 218 can be an O.D. measurement conducted at a wavelength of 600 nm (OD600 measurements) using a spectrophotometry device or system. The sample enumeration assay 218 can be conducted by devices or systems (e.g., a detector) communicatively coupled to the computing device 116, either directly or indirectly. The computing device 116 can record and store the results of such sample enumeration assays 218 in one or more databases stored in a memory of the computing device 116, a computing cloud, or a remote server accessible to the computing device 116.

The sample enumeration assays 218 can be conducted concurrently with the monitoring and recording of the changes in the solution characteristic of the reference samples 208. For example, O.D. measurements can be taken at the same time intervals 216 as measurements of the changes in the solution characteristics of the reference samples 208. As a more specific example, a sample enumeration assay 218 (e.g., an O.D. measurement) can be conducted on the reference sample 208 and a solution characteristic change of the same reference sample 208 can be recorded every 5 minutes. In other embodiments, the sample enumeration assays 218 can be conducted immediately before or immediately after changes in the solution characteristic of the reference samples 208 are recorded.

The method 200 can also comprise converting the results of the sample enumeration assays 218 to reference sample concentrations 220 using a conversion factor. For example, the results of O.D. measurements can be converted to reference sample concentrations 220 (expressed as CFU/mL) by multiplying the results of the O.D. measurements by a numerical conversion factor (e.g., O.D.$\times(1.76 \times 10^9)$). The conversion factors are usually instrument dependent and vary from instrument to instrument. The computing device 116 (or processors therein) or another device communicatively coupled to the computing device 116 can be programmed to convert the results of the sample enumeration assays 218 to reference sample concentrations 220 and store such reference sample concentrations 220 in one or more databases stored in a memory of the computing device 116, a computing cloud, or a remote server accessible to the computing device 116.

The method 200 can further comprise generating each of the multiple strain-specific LUTs 204 by associating the calculated reference sample concentrations 220 with changes in the solution characteristic of a particular reference sample 208 at specific time intervals 216 in step 2B.

For example, the strain-specific LUT 204 for SMa_CDC-27 can be generated by associating the calculated reference sample concentrations 220 for this particular reference sample 208 with the changes in the solution characteristic of the reference sample 208 measured every 5 minutes or every 10 minutes.

The method 200 can further comprise generating an averaged LUT 202 using data obtained from multiple strain-specific LUTs 204 in step 2C. As previously discussed, the averaged LUT 202 can refer to any of the species-specific LUT 210, the universal LUT 212, or another LUT organized by classification-type or characteristic. For example, the averaged LUT 202 can also be a Gram-positive LUT or a Gram-negative LUT. When the averaged LUT 202 is a species-specific LUT 210, the strain-specific LUTs 204 used to generate the species-specific LUT 210 can encompass different strains of the same species of the infectious agent. When the averaged LUT 202 is a universal LUT 212, the strain-specific LUTs 204 used to generate the universal LUT 212 can encompass different strains of infectious agents across different species.

In one embodiment, the averaged LUT 202 can be generated by taking an average of all solution characteristic change amounts 222 across multiple strain-specific LUTs 204 to yield a number of averaged solution characteristic change amounts 224. The averaged solution characteristic change amount 224 can be calculated for each predetermined reference sample concentration 220. For example, the predetermined reference sample concentrations 220 can comprise $1 \times 10^8$ CFU/mL, $2 \times 10^8$ CFU/mL, $3 \times 10^8$ CFU/mL, etc. In this example, the averaged LUT 202 can be generated by calculating each averaged solution characteristic change amount 224 from solution characteristic change amounts 222 obtained from multiple strain-specific LUTs 204.

Step 2C can further comprise associating each of the predetermined reference sample concentrations 220 with the results of the averaging calculations. For example, the averaged LUT 202 can be generated by associating the predetermined reference sample concentrations 220 with the averaged solution characteristic change amounts 224.

The averaged LUT 202 can be selected and retrieved based on information concerning a classification-type or characteristic of the infectious agent 106 in the source sample 104 (see, for example, FIG. 1A) or a lack of such information. For example, a species-specific LUT 210 for SMa can be selected and retrieved when the species of the infectious agent 106 in the source sample 104 is identified as SMa. Also, as an example, a universal LUT 212 can be selected and retrieved when the species of the infectious agent 106 in the source sample 104 has not been ascertained or is unknown. As additional examples, averaged LUTs 202 organized by genus, family, order, class, phylum, kingdom, or domain can also be selected and retrieved. Furthermore, averaged LUTs 202 organized by microbial characteristics, such as Gram-type, or functional capabilities, such as the ability to hydrolyze certain proteins or molecules, can also be selected or retrieved.

As previously discussed, the LUTs can be stored as part of a database software program in a memory of the computing device 116. In other embodiments, the LUTs can be stored as part of a database software program in a computing cloud or a remote server accessible to the computing device 116 over a network. The computing device 116 or one or more processors therein can search through hundreds or thousands of stored LUTs and select an appropriate LUT based on information concerning a classification-type (e.g., a species) or characteristic of the infectious agent 106 in the source sample 104.

Although method 200 is shown separate from method 100, it is contemplated by this disclosure and it should be understood by one of ordinary skill in the art that method 200 can be considered sub-steps or pre-steps of method 100. Moreover, the steps depicted in FIG. 2 do not require the particular order shown to achieve the desired result. Moreover, certain steps or processes may be omitted or occur in parallel in order to achieve the desired result. In addition, any of the systems or devices disclosed herein can be used in lieu of devices or systems shown in the steps of FIG. 2.

Figures 3A, 3B:
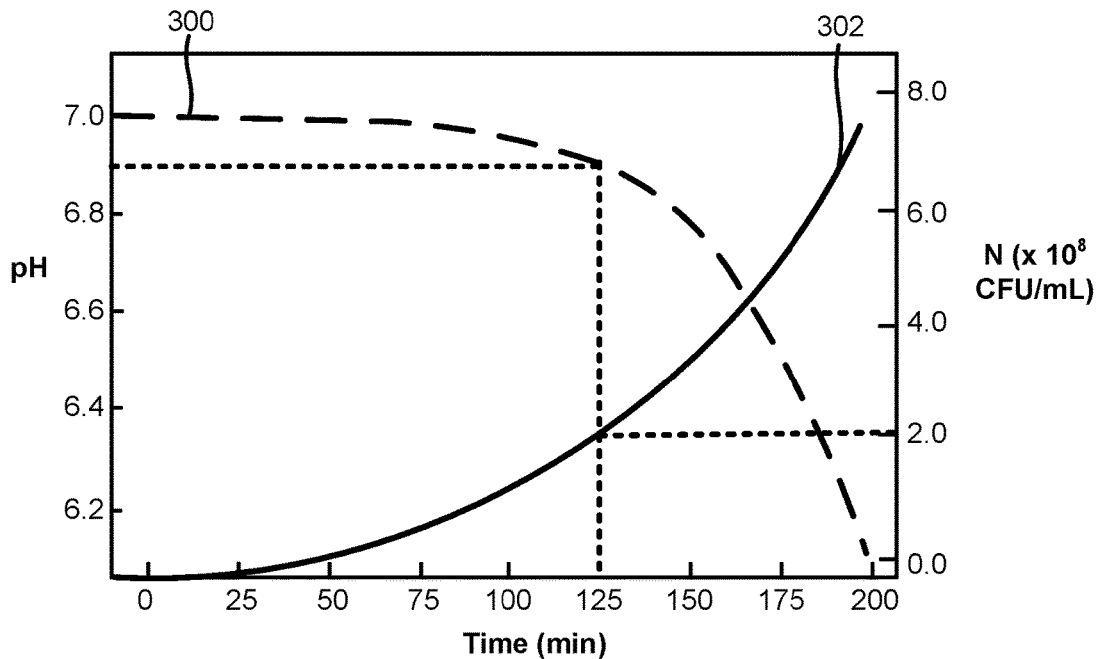
FIG. 3A illustrates example strain-specific look-up tables used to generate a species-specific look-up table.
FIG. 3B illustrates a pH growth curve and a reference concentration curve of a reference sample incubated over a period of time.

FIG. 3A illustrates example strain-specific LUTs 204 for various strains of SMa used to generate a species-specific LUT 210 for SMa. As shown in FIG. 3A, the strain-specific LUTs 204 can comprise a SMa_CDC-27 LUT, a SMa_CDC-91 LUT, a SMa_CDC-99 LUT, SMa_CDC-121 LUT, SMa_CDC-122 LUT, and a SMa_CDC-130 LUT. Although six strain-specific LUTs 204 are shown in the example embodiment of FIG. 3A, it is contemplated by this disclosure that an averaged LUT 202, such as a species-specific LUT 210 or a universal LUT 212, can be generated from at least three strain-specific LUTs 204. Increasing the number of strain-specific LUTs 204 can increase the accuracy of the averaged LUTs 202.

The strain-specific LUTs 204 can comprise reference sample concentrations 220 and solution characteristic change amounts 222. The solution characteristic change amounts 222 can be obtained from monitoring the change in the solution characteristic of a reference sample 208 comprising a strain of SMa over a period of time. For example, FIG. 3B illustrates a pH growth curve 300 representing the change in pH of a reference sample 208 comprising SMa_CDC-27.

The reference sample concentrations 220 can be obtained by converting results of sample enumeration assays 218 (see FIG. 2) performed on the reference sample 208 concurrently with monitoring the change in solution characteristic of the reference sample 208. For example, FIG. 3B illustrates a reference sample concentration curve 302 representing an increase in the infectious agent concentration within the reference sample 208 as measured by sample enumeration assays 218 performed on the reference sample 208 over time. As shown in FIG. 3B, the pH growth curve 300 and the reference sample concentration curve 302 can be plotted using the same x-axis (time in minutes).

Figures 3C, 3D:
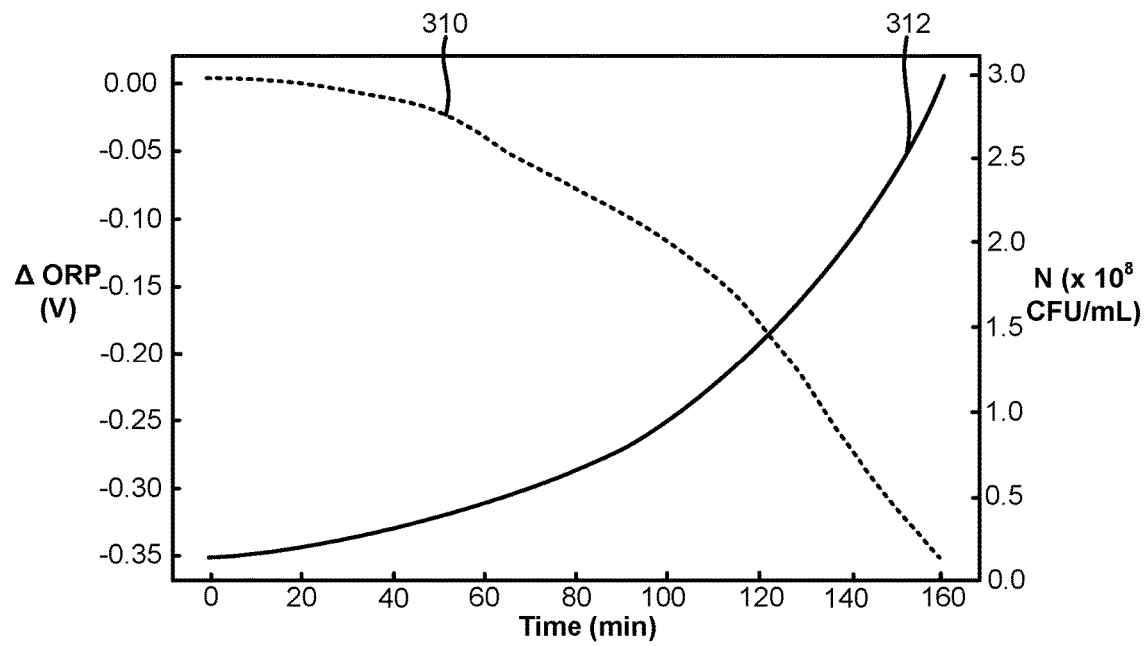
FIG. 3C illustrates additional example strain-specific look-up tables used to generate a species-specific look-up table.
FIG. 3D illustrates an ORP growth curve and a reference concentration curve of a reference sample incubated over a period of time.

FIG. 3C illustrates that a species-specific LUT 210 for the bacteria *Escherichia coli* (ECo) can be generated by taking an average of the solution characteristic change amounts 222 across various strain-specific LUTs 204 for ECo. Although specific species of infectious agents 106 are mentioned by name in FIGS. 3A and 3C (e.g., ECo and SMa) and their accompanying text descriptions, it is contemplated by this disclosure that the methods, systems, and devices disclosed herein can be used to generate output samples 102 from source samples 104 comprising any of the infectious agents 106 previously mentioned.

FIG. 3C illustrates example strain-specific LUTs 204 of various strains of ECo used to generate a species-specific LUT 210 for ECo. As shown in FIG. 3C, the strain-specific LUTs 204 can comprise an ECo PSC-18 LUT (for the PSC-18 strain of ECo), an ECo PSC-26 LUT (for the PSC-26 strain of ECo), an ECo PSC-66 LUT (for the PSC-66 strain of ECo), an ECo PSC-72 LUT (for the PSC-72 strain of ECo), an ECo CDC-13 LUT (for the CDC-13 strain of ECo), and an ECo CDC-19 LUT (for the CDC-19 strain of ECo). Although six strain-specific LUTs 204 are shown in the example embodiment of FIG. 3C, it is contemplated by this disclosure that an averaged LUT 202, such as a species-specific LUT 210 or a universal LUT 212, can be generated from between three and five strain-specific LUTs 204 or seven or more strain-specific LUTs 204. Increasing the number of strain-specific LUTs 204 can increase the accuracy of the averaged LUTs 202.

The strain-specific LUTs 204 can comprise reference sample concentrations 220 and solution characteristic change amounts 222. The solution characteristic change amounts 222 can be obtained from monitoring the change in the solution characteristic of a reference sample 208 comprising a strain of ECo over a period of time. The reference sample concentrations 220 can be obtained by converting results of sample enumeration assays 218 performed on the reference sample 208 (e.g., a reference sample comprising ECo) concurrently with monitoring the change in solution characteristic of the reference sample 208.

FIG. 3D illustrates an ORP growth curve 310 representing the change in the oxidation reduction potential of a reference sample 208 comprising ECo PSC-72. FIG. 3D also illustrates a reference sample concentration curve 312 representing an increase in the infectious agent concentration within a reference sample 208 comprising ECo as measured by sample enumeration assays 218 performed on the reference sample 208 over time. The ORP growth curve 310 and the reference sample concentration curve 312 can be plotted on the same graph using the same x-axis (time in minutes).

Figure 3E:
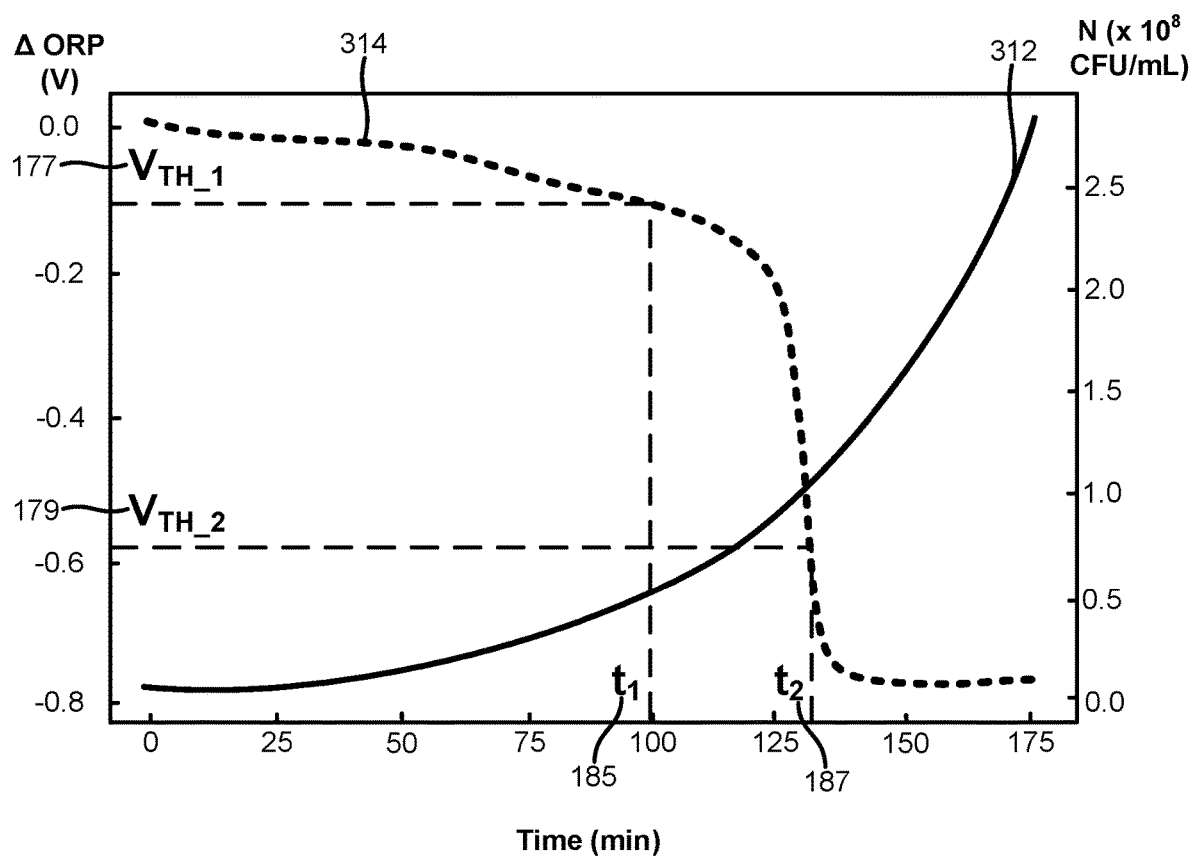
FIG. 3E illustrates a real-time ORP growth curve of a diluted sample and a reference concentration curve of a reference sample incubated over a period of time.

FIG. 3E illustrates a real-time ORP growth curve 314 (real-time ORP signal) representing the change in oxidation reduction potential of the diluted sample 112 comprising an infectious agent 106 identified as ECo. FIG. 3E also illustrates a reference sample concentration curve 312 representing an increase in the infectious agent concentration within a reference sample 208 comprising ECo as measured by sample enumeration assays 218 performed on the reference sample 208 over time. As shown in FIG. 3E, the real-time ORP growth curve 314 and the reference sample concentration curve 312 can be plotted on the same graph using the same x-axis (time in minutes).

FIG. 3E also illustrates that a first threshold time 185 ($t_1$) can be determined by monitoring the change in the solution characteristic of the diluted sample 112. The first threshold time 185 ($t_1$) can correspond to the amount of time elapsed for the solution characteristic of the diluted sample 112 to change by the first threshold amount 177. Moreover, FIG. 3E also illustrates that a second threshold time 187 ($t_2$) can also be determined by continuing to monitor the change in the solution characteristic of the diluted sample 112. The second threshold time 187 ($t_2$) can correspond to the amount of time elapsed for the solution characteristic of the diluted sample 112 to change by the second threshold amount 179. The computing device 116, the parameter analyzer 120, or a combination thereof can record the first threshold time 185 (or $t_1$) and the second threshold time 187 (or $t_2$) in a memory of the computing device 116 or another device or in a database accessible to the computing device 116 or another device.

Figure 4A:
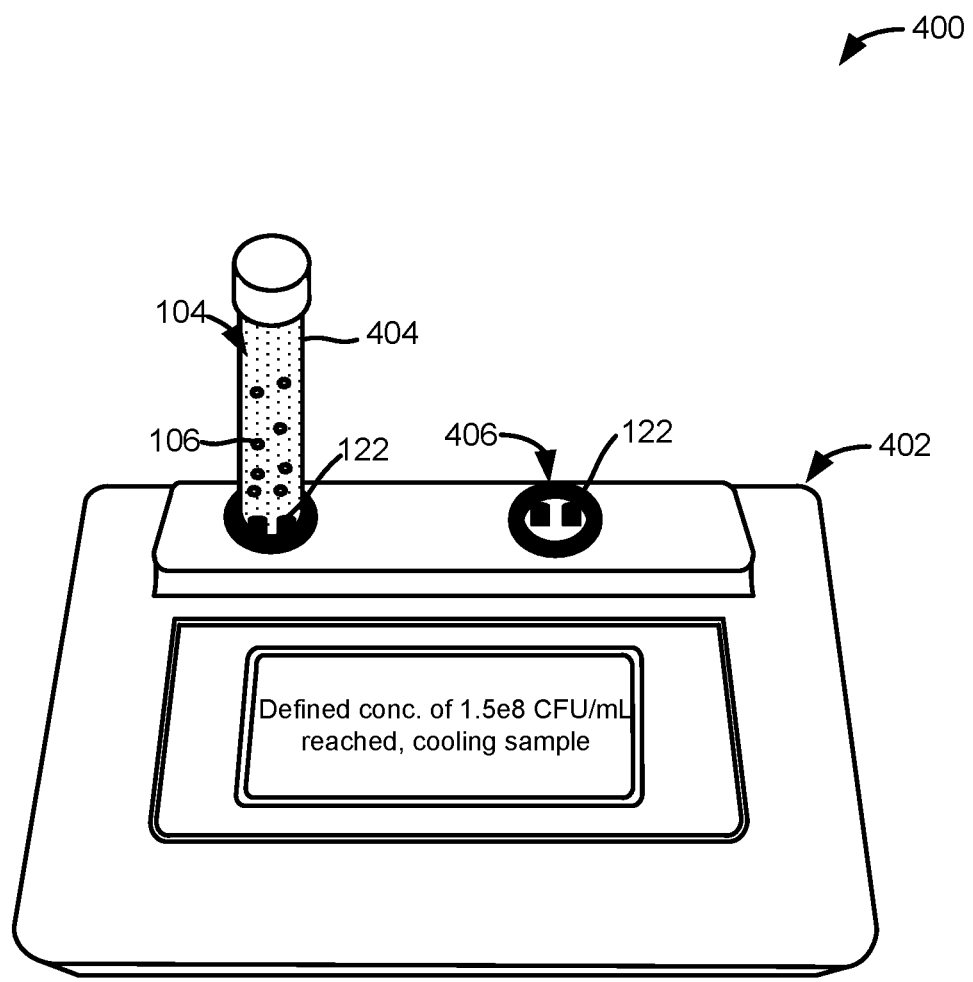
FIG. 4A illustrates one embodiment of a system for preparing an output sample for downstream testing.

FIG. 4A illustrates an example of a system 400 for preparing an output sample 102 from a source sample 104 comprising an infectious agent 106. More specifically, the system 400 can provide an output sample 102 comprising a defined concentration 105 of the infectious agent 106.

The system 400 can comprise a sample preparation apparatus 402 that integrates the functionality of the computing device 116, the parameter analyzer 120, and the sensor 122.

The system 400 can undertake any of the steps of method 100 of FIG. 1A or FIG. 1B. For example, one or more processors within the sample preparation apparatus 402 can undertake any of the steps 1C, 1D, or 1E of method 100.

In addition, the system 400 can comprise one or more reaction vessels 404 compatible with the sample preparation apparatus 402. For example, the source sample 104 can be introduced into a reaction vessel 404 and the reaction vessel 404 can be placed or positioned within a vessel receiving space 406 of the sample preparation apparatus 402.

Figure 4B:
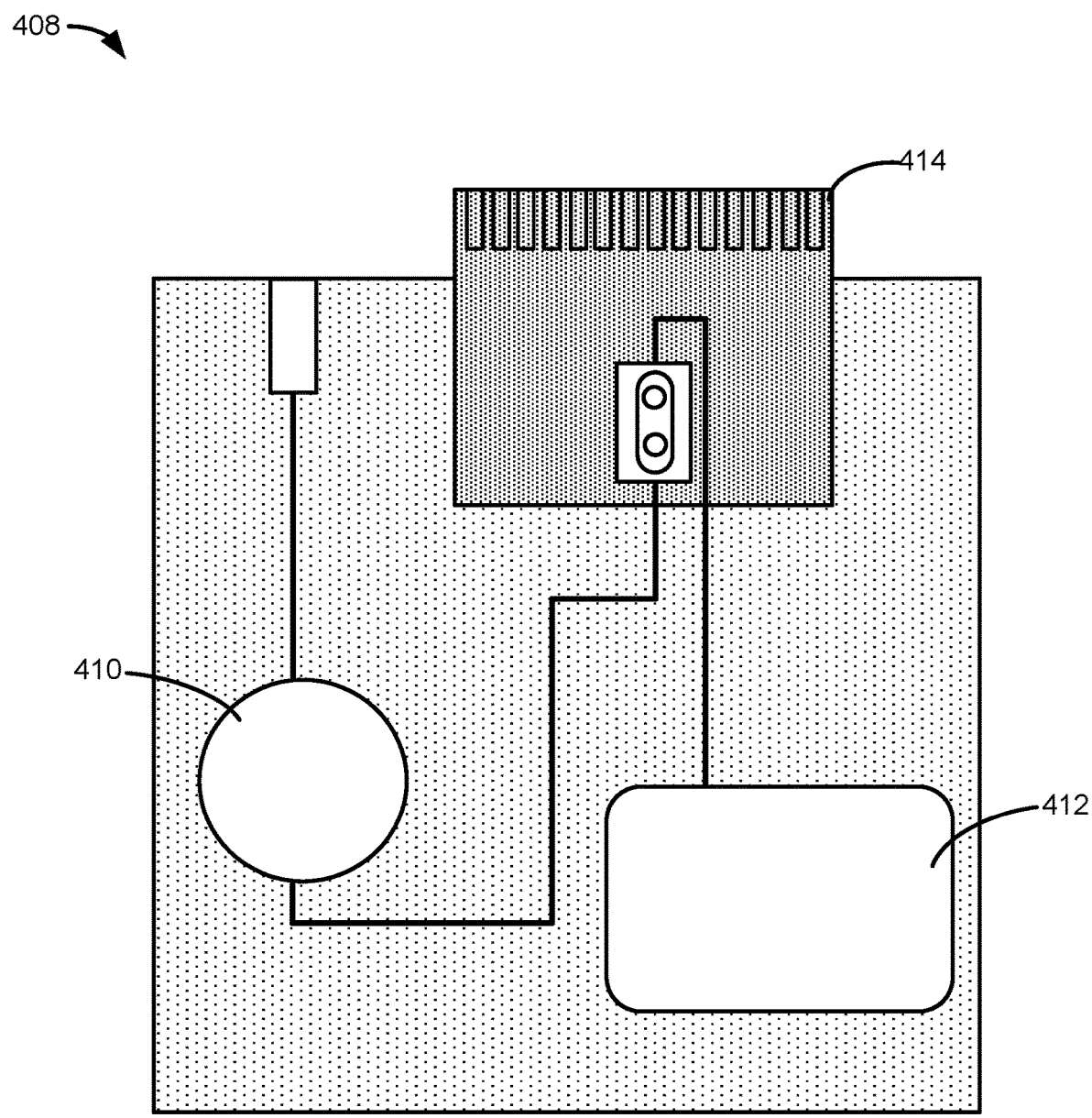
FIG. 4B illustrates one embodiment of a test cartridge for use with certain apparatus and systems disclosed herein.

In another embodiment shown in FIG. 4B, a test cartridge 408 can be used instead of or in addition to the reaction vessel 404. The test cartridge 408 can comprise a sample receiving surface 410 or space and a sample output surface 412 or space. The sample receiving surface 410 or space of the test cartridge 408 can receive an aliquot of the source sample 104 and the output sample 102 can be injected, pumped, or otherwise introduced into the sample output surface 412 or space. The test cartridge 408 can interface with the sample preparation apparatus 402 via a cartridge interface 414. The cartridge interface 414 can be an electronic interface, such as a Universal Serial Bus (USB) interface, a high-speed serial computer expansion bus interface, or a combination thereof, configured to allow the sample preparation apparatus 402 to read or retrieve information from the test cartridge 408. In embodiments where the test cartridge 408 is used instead of a reaction vessel 404, the vessel receiving space 406 can be configured as a cartridge receiving slot or space.

In one embodiment, a user can begin the process of obtaining an output sample 102 from a source sample 104 by placing the reaction vessel 404 (or the test cartridge 408) comprising the source sample 104 into the vessel receiving space 406 (or the cartridge receiving slot) of the sample preparation apparatus 402 and inputting a defined concentration 105 in the sample preparation apparatus 402. For example, the defined concentration 105 can be a concentration of 3e8 or 5e5 CFU/mL. The defined concentration 105 can be inputted through an input component of the sample preparation apparatus 402 such as a keyboard, a touchscreen, or a combination thereof. In other embodiments, the defined concentration 105 can be inputted through a computing device (such as a mobile device or a laptop) communicatively coupled to the sample preparation apparatus 402 and the defined concentration 105 can be transmitted to the sample preparation apparatus 402.

In another embodiment, a user can begin the process of obtaining the output sample 102 from the source sample 104 by inputting or otherwise providing information concerning the classification (e.g., species, family, order, etc.) or characteristic (Gram-positive or Gram-negative) of the infectious agent 106 within the source sample 106 and the system 400 can determine the defined concentration 105 of the output sample 102 needed for any downstream testing.

In some embodiments, one or more metering conduits within the sample preparation apparatus 402 can then dilute the source sample 104 by introducing a dilutive solution 114 to the source sample 104 to yield the diluted sample 112. The metering conduits can refer to channels, passageways, capillaries, tubes, or a combination thereof within the sample preparation apparatus 402. The metering conduits can also refer to channels (e.g., microfluidic channels), passageways, capillaries, or tubes serving as part of hydraulic pump, a pneumatic pump, peristaltic pump, a vacuum or positive pressure pump, a manual or mechanical pump, a syringe pump, or a combination thereof within the sample preparation apparatus 402.

In one embodiment, the source sample 104 can be drawn or pumped (e.g., through vacuum pressure) from the reaction vessel 404 into channels, passageways, capillaries, tubes, or a combination thereof within the sample preparation apparatus 402. In this embodiment, the dilutive solution 114 can be introduced to the source sample 104 once the source sample 104 has been drawn or pumped from the reaction vessel 404. In other embodiments, the test cartridge 408 can comprise channels, conduits, or capillaries for pumping or delivering the diluted sample 112, the dilutive solution 114, the source sample 104, the output sample 102, or a combination thereof.

In other embodiments, the source sample 104 can remain within the reaction vessel 404 (or the test cartridge 408) and the dilutive solution 114 can be introduced into the reaction vessel 404 (or the test cartridge 408) through one or more ports along a base, top, or side of the reaction vessel 404. In other embodiments, the dilutive solution 114 can be introduced into the reaction vessel 404 (or the test cartridge 408) through one or more ports defined on a cap or cover of the reaction vessel 404.

In other embodiments, the source sample 104 can be diluted by the dilutive solution 114 prior to placement into the sample preparation apparatus 402.

In some embodiments, at least a portion of the sensor 122 can extend into or be in fluid communication with the diluted sample 112 within the reaction vessel 402 (or within or on the test cartridge 408). For example, the electrodes (e.g., the active electrode and the reference electrode) can extend into or be in fluid communication with the diluted sample 112 through ports along the base of the reaction vessel 404 (or the test cartridge 408). In other embodiments where the source sample 104 or the diluted sample 112 is drawn or directed into the sample preparation apparatus 402, the diluted sample 112 can be introduced to the sensor 122 within the sample preparation apparatus 402 via one or more fluid delivery conduits such as channels (e.g., microfluidic channels), passageways, capillaries, or tubes within the sample preparation apparatus 402.

In some embodiments, the sensor 122 of the sample preparation apparatus 402 can be a pH sensor comprising a reference electrode and an active electrode. In these embodiments, the active electrode can comprise a functionalization (or pH-active) layer 508 (see FIGS. 5A and 5B).

In other embodiments, the sensor 122 of the sample preparation apparatus 402 can be an ORP sensor comprising a reference electrode and an active electrode. In these embodiments, the active electrode can comprise a redox-active layer 610 (see FIGS. 6A and 6B). As will be discussed in more detail, the redox-active layer 610 can comprise a metal layer or metal electrode.

In yet additional embodiments, the sensor 122 of the sample preparation apparatus 402 can be a combined pH and ORP sensor comprising multiple reference electrodes and active electrodes. In these embodiments, at least one active electrode can comprise the redox-active layer 712 and at least another active electrode can comprise the functionalization layer 716 (see FIGS. 7A and 7B).

In some embodiments not shown in the figures, the sensor 122 (or parts therein) can be integrated within the test cartridge 408. For example, the diluted sample 112 or the source sample 104 can be in fluid communication with the functionalization (or pH-active) layer or the redox-active layer and a reference electrode of the sensor 122 by virtue of the diluted sample 112 or the source sample 104 being introduced on the sample receiving surface 410. In other examples, at least part of the test cartridge 408 can be immersed within the diluted sample 112.

One or more processors within the sample preparation apparatus 402 can be programmed to retrieve an averaged LUT 202 such as a species-specific LUT 210 based on information concerning a species of the infectious agent 106 in the source sample 104. In other embodiments, the one or more processors within the sample preparation apparatus 402 can be programmed to retrieve a universal LUT 212 or another type of inter-species LUT based on a lack of information concerning the infectious agent 106 in the source sample 104.

The LUTs can be stored as part of a database software program in a memory of the sample preparation apparatus 402. In other embodiments, the LUTs can be stored as part of a database software program in a computing cloud or a remote server accessible to the sample preparation apparatus 402 over a network. One or more processors of the sample preparation apparatus 402 can be programmed to search through hundreds or thousands of stored LUTs to select an appropriate LUT based on a classification-type (e.g., a species) or characteristic of the infectious agent 106 in the source sample 104.

The one or more processors of the sample preparation apparatus 402 can be programmed to set a threshold amount 118 based on the defined concentration 105 and data from the averaged LUT 202. For example, the defined concentration 105 can be inputted by the user into the sample preparation apparatus 402 as 3e8 or 5e5 CFU/mL. The one or more processors of the sample preparation apparatus 402 can be programmed to select the averaged solution characteristic change amount 224 of $\Delta$pH −0.20 as the threshold amount 118 since such a solution characteristic change amount is associated with a reference sample concentration 220 of 3e8 or 5e5 CFU/mL.

The sample preparation apparatus 402 can also comprise an incubating component to incubate the diluted sample 112 to the incubation temperature 124 of between approximately 30° C. and 40° C. (or about 35° C.±2° C.). For example, the incubating component can incubate the diluted sample 112 within the reaction vessel 404 or incubate the diluted sample 112 drawn or pumped into the sample preparation apparatus 402. In other embodiments, the incubating component can incubate the entire test cartridge 408 or a portion therein comprising the diluted sample 112.

The sample preparation apparatus 402 can monitor a change in the solution characteristic (e.g., a pH or ORP) of the diluted sample 112 while the diluted sample 112 is being incubated. The sensor 122 of the sample preparation apparatus 402 can be configured to respond to a change in the solution characteristic (e.g., the pH or ORP) of the diluted sample 112. The solution characteristic of the diluted sample 112 can be monitored in the absence of any exogenous reporter molecules added to the diluted sample 112.

The sample preparation apparatus 402 can comprise a cooling component to cool the diluted sample 112. The cooling component can cool the diluted sample 112 to a cooling temperature 126 when the solution characteristic of the diluted sample 112 changes by the threshold amount 118. The diluted sample 112 can be cooled when the concentration of the infectious agent 106 within the diluted sample 112 reaches the defined concentration 105.

The cooling temperature 126 can be between approximately 4° C. and 25° C. In some embodiments, the cooling temperature 126 can be between approximately 4° C. and 15° C.

In some embodiments, the sample preparation apparatus 402 can cool the same reaction vessel 404 comprising the diluted sample 112. In these embodiments, the now cooled diluted sample 112 within the same reaction vessel 404 can be considered the output sample 102 when the concentration of the infectious agent 106 within the reaction vessel 404 reaches the defined concentration 105.

In other embodiments, the cooling component can cool the entire test cartridge 408 or a portion therein comprising the diluted sample 112. In these embodiments, the now cooled diluted sample 112 within the test cartridge 408 can be considered the output sample 102 when the concentration of the infectious agent 106 within the test cartridge 408 reaches the defined concentration 105.

In other embodiments, the diluted sample 112 can be introduced, pumped, or otherwise transferred to a different reaction vessel 404 (or a different part of the test cartridge 408) to be cooled. In these embodiments, the cooled diluted sample 112 within the different reaction vessel 404 (or the different part of the test cartridge 408, such as the sample output surface 412 or space) can be considered the output sample 102.

In one embodiment, sample preparation apparatus 402 can alert a user that the solution characteristic of the diluted sample 112 has changed by the threshold amount 118 and that the infectious agent 106 within the reaction vessel 404 (or within the test cartridge 408) has reached the defined concentration 105. For example, the sample preparation apparatus 402 can generate an audible alert, a visual or graphic alert, a haptic or motion alert, or a combination thereof. As a more specific example, the sample preparation apparatus 402 can generate a message on a display component informing a user that the output sample 104 is ready for retrieval or for use in a downstream test.

Although FIG. 4A shows one embodiment of the sample preparation apparatus 402 as a benchtop apparatus, it is contemplated by this disclosure and it should be understood by one of ordinary skill in the art that the sample preparation apparatus 402 or components therein can be implemented as a cartridge, a test strip, a micro-electro-mechanical system (MEMS) device, lab-on-a-chip (LOC) device, a microfluidic chip, or a combination thereof.

In addition, although FIG. 4A shows the sample preparation apparatus 402 having two vessel receiving spaces 406 (or two cartridge receiving slots), it is contemplated by this disclosure and it should be understood by one of ordinary skill in the art that the sample preparation apparatus 402 can have one vessel receiving space 406 (or one cartridge receiving slot) or three or more vessel receiving spaces 406 406 (or three or more cartridge receiving slots). In the embodiment where the sample preparation apparatus 402 comprises multiple vessel receiving spaces 406 (or multiple cartridge receiving slots), the sample preparation apparatus 402 can be considered a multiplex device. Moreover, although FIG. 4B shows the test cartridge 408 comprising one sample receiving surface 410 or space and one sample output surface 412 or space, it is contemplated by this disclosure that the test cartridge 408 can comprise two or more sample receiving surfaces 410 or spaces (to receive two or more source samples 104) and two or more sample output surfaces 412 or spaces (to accommodate two or more output samples 102).

Figure 5A:
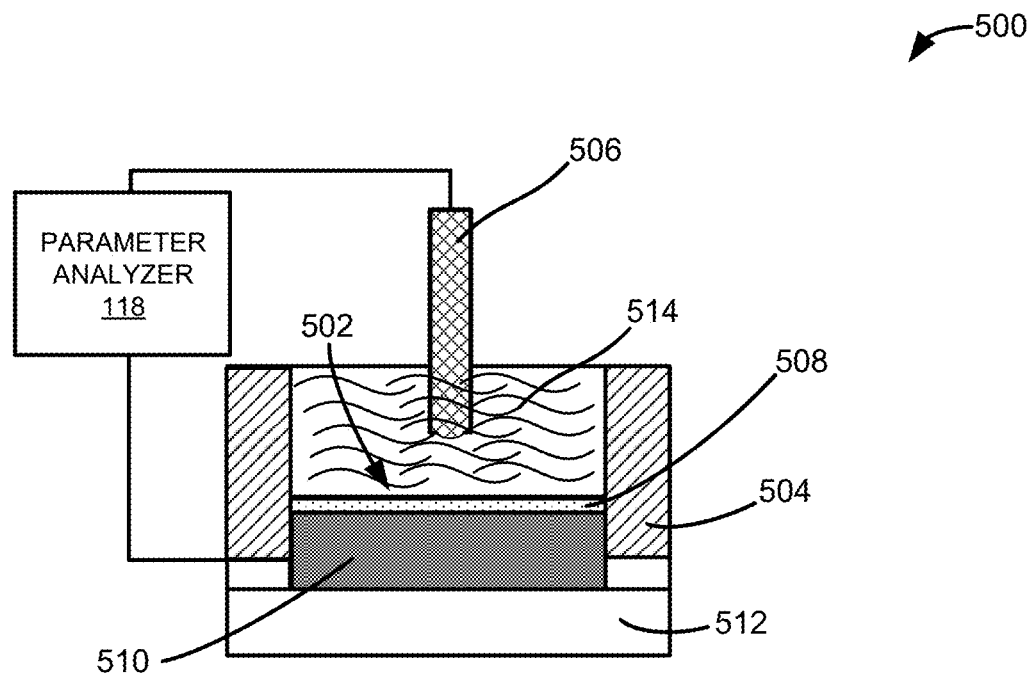
FIG. 5A illustrates a schematic of one embodiment of a pH sensor used as part of the methods and systems described herein.

FIG. 5A illustrates a schematic of one embodiment of a pH sensor 500 used as part of the methods and systems described herein. The sensor 500 of FIG. 5A can be or refer to any of the sensors 122 depicted in FIG. 1A, 1B, 2, 4A, or 4B. The sensor 500 can be or comprise an electrochemical cell comprising container walls 504, an active electrode 502 positioned on a substrate layer 512, and an external reference electrode 506. The active electrode 502 can comprise a functionalization layer 508 and a conductor layer 510. The sensor 500 can be configured to receive or be in fluid contact with a solution 514. For example, the sensor 500 can receive and retain the solution 514 within the container walls 504 as shown in FIG. 5A. In other embodiments not shown in the figures but contemplated by this disclosure, one or more layers of the sensor 500 can be in fluid contact with the solution 514 even though the solution 514 is not retained within the container walls 504 of the sensor 500 or the sensor 500 has no container walls 504.

In all such embodiments, the solution 514 can be any of the diluted samples 112 or the reference samples 208 or aliquots thereof. The sensor 500 can be connected or coupled to the parameter analyzer 120. In one embodiment, the parameter analyzer 120 can be coupled to both the external reference electrode 506 and the active electrode 510. In other embodiments, the parameter analyzer 120 can be coupled to the external reference electrode 506, the conductor layer 510, as well as other layers. As shown in FIG. 5A, the external reference electrode 506 can extend into the solution 514.

When the parameter analyzer 120 is coupled to the external reference electrode 506, the conductor layer 510, or another layer, the parameter analyzer 120 can measure a difference in the electrical characteristic of the solution 514. The external reference electrode 506 can have a stable and well-known internal reference potential and can also act as a differential noise filter for removing electrical noise from measurements taken by the sensor 500. An operator or clinician can use this setup to determine or record a relative change in the electrical characteristic of the sensor 500 rather than having to ascertain an absolute change. An operator or clinician can also use the external reference electrode 506 to determine or record a relative difference between the electrical characteristics of multiple sensors 500. In one embodiment, the external reference electrode 506 can be a standalone probe or electrode. In other embodiments, the external reference electrode 506 can be coupled to the parameter analyzer 120 or a computing device 116 (not shown) connected to the parameter analyzer 120. The parameter analyzer 120 can also be used to apply a voltage or current to the active electrodes and the external reference electrode 506.

In one embodiment, the external reference electrode 506 can be a silver/silver chloride (Ag/AgCl) electrode. In other embodiments, the external reference electrode 506 can comprise a saturated calomel reference electrode (SCE) or a copper-copper (II) sulfate electrode (CSE).

The substrate layer 512 can comprise any non-conducting material such as a polymer, an oxide, a ceramic, or a composite thereof. As depicted in FIG. 5A, the conductor layer 510 can be disposed on or cover the substrate layer 512.

The conductor layer 510 can comprise a metal, a semi-conducting material, a metal/metal-salt, or a combination thereof. For example, the conductor layer 510 can comprise silicon, gold, silver, aluminum, platinum, or a composite thereof. The conductor layer 510 can also be an organic semiconductor, a carbon nanotube, graphene, an organic conductor such as those derived from polyacetylene, polyaniline, Quinacridone, Poly(3,4-ethylenedioxythiophene) or PEDOT, PEDOT: polystyrene sulfonate (PSS), or a combination thereof. The conductor layer 510 can be composed of any conducting material which allows an electrical property change to be measured, including, but is not limited to, a voltage change, a capacitance change, a conductance change, and/or a current change measured through the conductor layer 510, the functionalization layer 508, and the solution 514 to the external reference electrode 506.

As depicted in FIG. 5A, the functionalization layer 508 can be disposed on or cover the conductor layer 510. The functionalization layer 508 can comprise oxides, silanes, DNA, proteins, antibodies, self-assembled mono layers (SAMs), oxides, buffered hydrogels, PVC, parylene, polyACE, or any other biochemically active materials. The functionalization layer 508 can be configured to facilitate the sensor 500 from interacting with ions, analytes, or other molecules or byproducts in the solution 514. For example, the functionalization layer 508 can be a pH-sensitive layer or pH-active layer.

In one example, the functionalization layer 508 can comprise hydroxyl groups which can interact with hydrogen ions ($H^+$) in the solution 514. This interaction can generate a change in the electrical characteristic between the sensor 500 and the external reference electrode 506 as detected by the parameter analyzer 120. In one embodiment, this interaction can create a measurable change in the electrical characteristic of the sensor 500 at the interface between the solution 514 and the functionalization layer 508 or the interface between the solution 514 and the conductor layer 510.

For example, the parameter analyzer 120 can be a voltmeter and the voltmeter can detect a voltage (potential) change ($\Delta V$) at or near the functionalization layer 508 between the active electrode 502 and the external reference electrode 506 exposed to the solution 514. The voltage change can be determined with respect to the external reference electrode 506 extending into or in contact with the solution 514. In this embodiment, the functionalization layer 508 and the conductor layer 510 can be considered part of a working or active electrode 502.

As depicted in FIG. 5A, the solution 514, the functionalization layer 508, and the conductor layer 510 can be surrounded by the container walls 504. The container walls 504 can be made of an inert or non-conductive material. The container walls 504 can comprise, but is not limited to, a polymeric material such as polyvinyl chloride (PVC), poly (methyl methacrylate) (PMMA), polydimethylsiloxane (PDMS), a ceramic, glass, or a combination thereof.

Figure 5B:
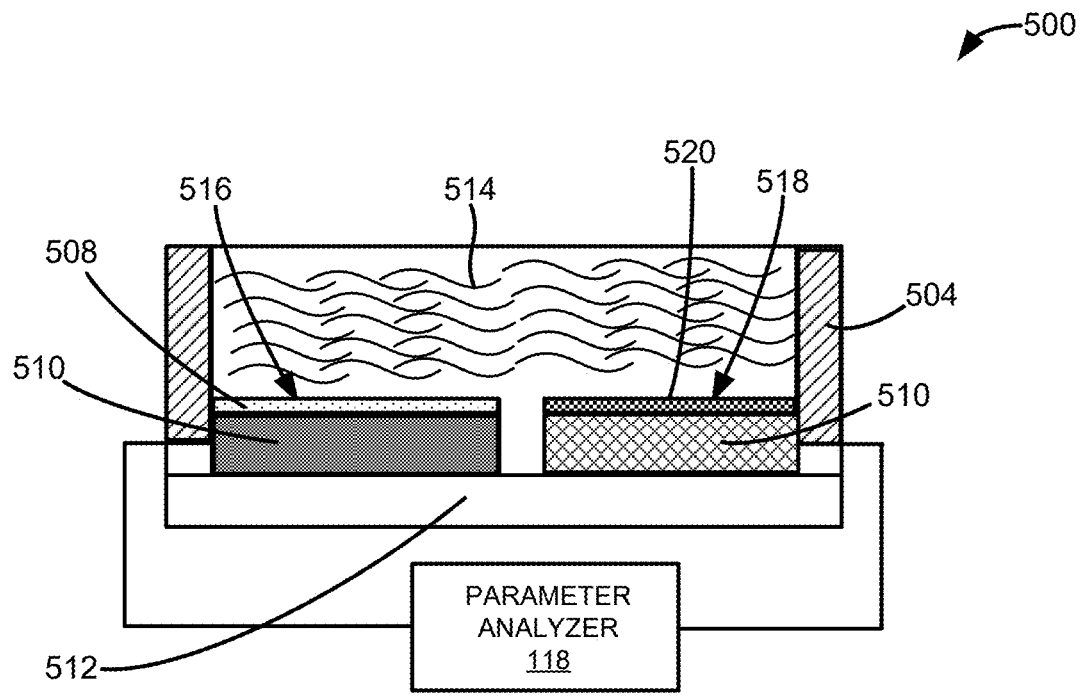
FIG. 5B illustrates a schematic of another embodiment of the pH sensor used as part of the methods and systems described herein.

FIG. 5B illustrates a schematic of another embodiment of the pH sensor 500 used as part of the methods and systems described herein. The sensor 500 can be or refer to any of the sensors 122 depicted in FIG. 1A, 1B, 2, 4A, or 4B.

In this embodiment, the sensor 500 can comprise an active electrode 516 or an indicator electrode and an on-chip reference electrode 518. In this embodiment, the active electrode 516 (i.e., the active electrode) and the on-chip reference electrode 518 can be disposed on the same substrate layer 512. The substrate layer 512 can be composed of the same material as the substrate layer 512 depicted in FIG. 5A.

The solution 514 can flow over or be exposed to both the active electrode 516 and the on-chip reference electrode 518 simultaneously. In this embodiment, the active electrode 516 and the on-chip reference electrode 518 can be separated by a container wall 504 or container divide.

The active electrode 516 can comprise the functionalization layer 508 disposed on or covering the conductor layer 510. The functionalization layer 508 can comprise oxides, silanes, DNA, proteins, hydroxyl group, antibodies, oxides, self-assembled mono layers (SAMs), buffered hydrogels, PVC, parylene, polyACE, or any other biochemically active materials.

As shown in FIG. 5B, a passivation layer 520 can be disposed on or cover the conductor layer 510. The passivation layer 520 can be configured to prevent the on-chip reference electrode 518 from interacting with analytes, ions, or other molecules or byproducts in the solution 514. For example, the passivation layer 520 can be a pH-insensitive layer. The passivation layer 520 can comprise silanes, self-assembled monolayers (SAMs), buffered hydrogels, parylene, polyACE, or any other biochemically inert material.

In this embodiment, the parameter analyzer 120 can have a lead connection wire, such as a copper wire, connected to the conductor layer 510 of the active electrode 516 and another lead connection wire connected to the conductor layer 510 of the on-chip reference electrode 518. The parameter analyzer 120 can also be used to apply a voltage or current to the active electrodes and the on-chip reference electrode 518.

In this and other embodiments, the sensor 500 shown in FIG. 5B miniaturizes the sensor set-up shown in FIG. 5A. The on-chip reference electrode 518 obviates the need for an external reference electrode, such as the external reference electrode 506. The on-chip reference electrode 518 can also be a silver/silver chloride (Ag/AgCl) electrode. In other embodiments, the on-chip reference electrode 518 can be, but is not limited to, a saturated calomel reference electrode (SCE) or a copper-copper (II) sulfate electrode (CSE). The on-chip reference electrode 518 provides similar functionality as that of the external reference electrode 506 in this embodiment of the sensor 500. The passivation layer 520 of the on-chip reference electrode 518 prevents the conductor layer 510 covered by the passivation layer 520 from interacting with the ions, analytes, or other molecules or byproducts in the solution 514. This allows a reader or another device from being able to differentiate the electrical signals obtained by the parameter analyzer 120. In some embodiments, the passivation layer 520 can refer to an on-chip reference electrode 518 with a well-defined potential. In other embodiments, the on-chip reference electrode 518 can be without a passivation layer 520.

In one embodiment where the conductor layer 510 is used as a reference electrode, the conductor layer 510 can be a metal covered with a metal salt such as a metal chloride. In another embodiment, the conductor layer 510 can also be covered with an oxide. For example, the conductor layer 510 can be a silver/silver chloride contact. In this embodiment, the conductor layer 510 can be covered by, but is not limited to, a passivation layer 520 such as a KCL electrolyte gel or KCL solution, to prevent the conductor layer 510 from interacting with analytes, ions, or other molecules or byproducts in the solution 514 and to act as a reference electrode. In other embodiments, the on-chip reference electrode 518 can be covered by a miniaturized cell that stabilizes a small internal potential similar to a calomel electrode or an Ag/AgCl electrode.

Figure 6A:
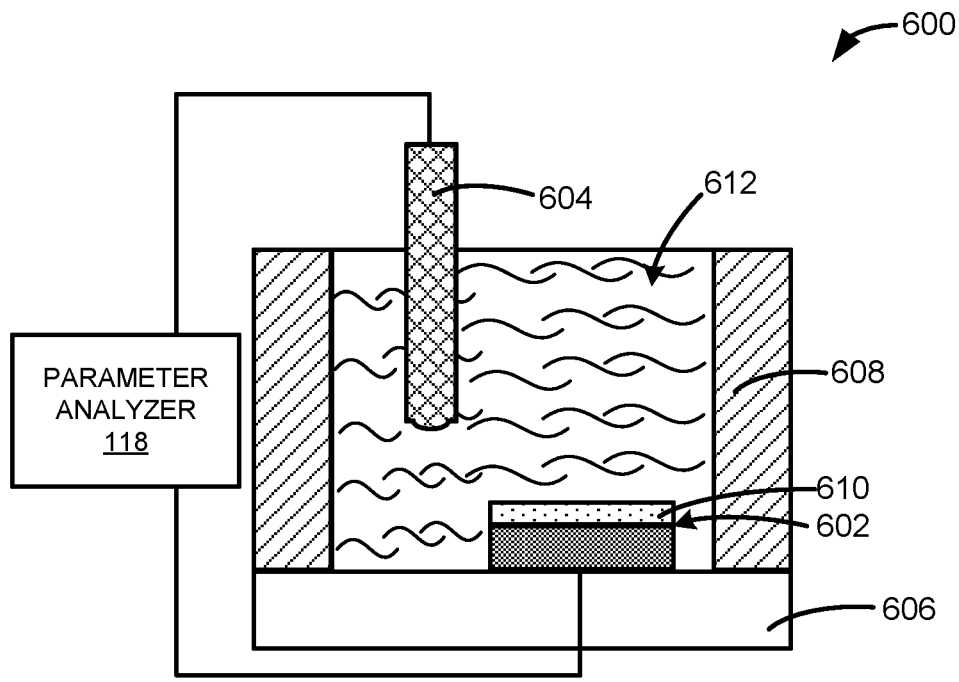
FIG. 6A illustrates a schematic of one embodiment of an ORP sensor used as part of the methods and systems described herein.

FIG. 6A illustrates a schematic of one embodiment of an ORP sensor 600 used as part of the methods and systems described herein. The sensor 600 of FIG. 6A can be or refer to any of the sensors 122 depicted in FIG. 1A, 1B, 2, 4A, or 4B. The sensor 600 can be an electrochemical cell comprising an active electrode 602 and an external reference electrode 604. In some embodiments of the sensor 600, the active electrode 602 and the external reference electrode 604 are the only electrodes of the sensor 600.

The active electrode 602 can extend from or be disposed on a substrate layer 606. The substrate layer 606 can comprise any non-conducting material such as a polymer, an oxide, a ceramic, or a composite thereof. The electrochemical cell can be surrounded or contained by walls 608 configured to retain a sampled solution 612. The walls 608 can be made of an inert or non-conductive material.

The sampled solution 612 can refer to any of the diluted samples 112 or the reference samples 208 or an aliquot thereof. At least part of the external reference electrode 604 and the active electrode 602 can be in fluid communication or in fluid contact with the sampled solution 612. For example, the external reference electrode 604 can extend into or be immersed in the sampled solution 612. The external reference electrode 604 can also have a stable or well-known internal voltage and the sensor 600 can use the external reference electrode 604 to determine or measure a relative change in the potential of the active electrode 602. In one embodiment, the external reference electrode 604 can be a standalone probe or electrode. In other embodiments, the external reference electrode 604 can be coupled to the parameter analyzer 120. In some embodiments, multiple sensors (including but not limited to the first sensor and the second sensor) can share and use the same external reference electrode 604.

In one embodiment, the external reference electrode 604 can be a silver/silver chloride (Ag/AgCl) electrode. In other embodiments, the external reference electrode 604 can comprise a saturated calomel reference electrode (SCE) or a copper-copper (II) sulfate electrode (CSE). The external reference electrode 604 can also be a pseudo-reference electrode including any metal that is not part of the active electrode such as platinum, silver, gold, or a combination thereof; any metal oxide or semiconductor oxide material such as aluminum oxide, iridium oxide, silicon oxide; or any conductive polymer electrodes such as polypyrrole, polyaniline, polyacetylene, or a combination thereof.

The active electrode 602 can comprise multiple conductive layers (e.g., a stack of metallic layers) and a redox-active layer 610 or layer such as a gold layer, a platinum layer, a metal oxide layer, a carbon layer, or a combination thereof on top of the multiple conductive layers. In some embodiments, the metal oxide layer can comprise an iridium oxide layer, a ruthenium oxide layer, or a combination thereof. The parameter analyzer 120 can be coupled to the active electrode 602 and the external reference electrode 604.

The parameter analyzer 120, the computing device 116, or a combination thereof can determine the ORP of the sampled solution 612 by measuring the potential difference between the external reference electrode 604 and the active electrode 602 instantly or over a period of time. As shown in FIG. 6A, the parameter analyzer 120 can be a voltmeter or any other type of high-impedance amplifier or sourcemeter. The voltmeter can measure a relative change in an equilibrium potential at an interface between the redox-active layer 610 of the active electrode 602 and the sampled solution 612 containing electro-active redox species. The parameter analyzer 120 can also be used to apply a voltage or current to the active electrodes and the external reference electrode 604.

The solution characteristic of the sampled solution 612 can change as the amount of electro-active redox species changes due to pathogen metabolism-related energy build-up and breakdown or oxygen-depletion or release. For example, the amount of electro-active redox species in the sampled solution 612 can change as a result of cellular activity undertaken by the infectious agents in solution. As a more specific example, the amount of electron donors from Table 1 (e.g., the amount of energy carriers such as nicotinamide adenine dinucleotide (NADH) and flavin adenine dinucleotide ($FADH_2$)) in the sampled solution 612 can change due to the growth of the infectious agents in solution. Also, as another more specific example, the amount of oxygen depleted in the sampled solution 612 can change due to the growth of the infectious agents in solution.

In one embodiment, the active electrode 602 can comprise a metallic layer. The metallic layer can comprise a gold layer, a platinum layer, or a combination thereof. The active electrode 602 can also comprise multiple layers comprising a semiconductor layer having a redox-active metal oxide layer, such as iridium oxide or ruthenium oxide on top of the multiple layers. In other embodiments, the active electrode 602 can comprise one or more metallic layers, one or more redox-active metal oxide layers, one or more semiconductor layers, or any combination or stacking arrangement thereof.

Figure 6B:
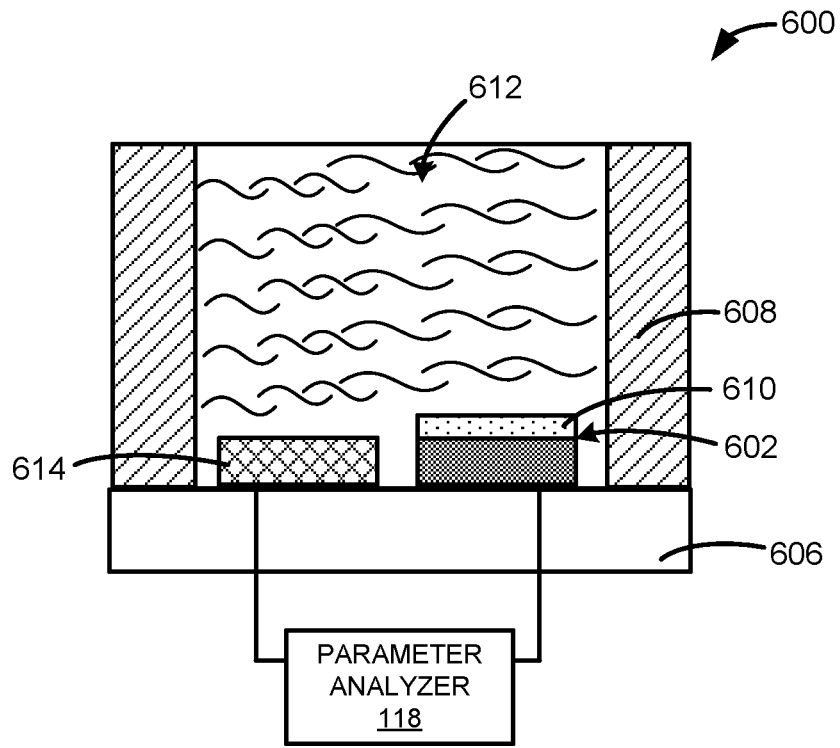
FIG. 6B illustrates a schematic of another embodiment of the ORP sensor used as part of the methods and systems described herein.

FIG. 6B illustrates a schematic of another embodiment of an ORP sensor 600 used as part of the methods and systems described herein. The sensor 600 of FIG. 6B can be or refer to any of the sensors 122 depicted in FIG. 1A, 1B, 2, 4A, or 4B. The sensor 600 can have an on-chip reference electrode 614 disposed on the substrate layer 606 in lieu of the external reference electrode 604 of FIG. 6A. In some embodiments of the sensor 600, the active electrode 602 and the on-chip reference electrode 614 are the only electrodes of the sensor 600. The parameter analyzer 120 can also be used to apply a voltage or current to the active electrodes and the on-chip reference electrode 614.

In these and other embodiments, the on-chip reference electrode 614 can be coated by a polymeric coating. For example, the on-chip reference electrode 614 can be coated by a polyvinyl chloride (PVC) coating, a perfluorosulfonate coating (e.g., Nafion™), or a combination thereof.

The on-chip reference electrode 614 can serve the same purpose as the external reference electrode 604 except be fabricated on or integrated with the substrate layer 606. The on-chip reference electrode 614 can be located adjacent to or near the active electrode 602. The sensor 600 of FIG. 6B can serve the same function as the sensor 600 of FIG. 6A. Similar to the active electrode 602 of FIG. 6B, the on-chip reference electrode 614 can also be in fluid communication or contact with the sampled solution 612 retained within walls 608.

The on-chip reference electrode 614 can be comprised of a metal, a semiconductor material, or a combination thereof. The metal of the on-chip reference electrode 614 can be covered by an oxide layer, a silane layer, a polymer layer, or a combination thereof. In another embodiment, the on-chip reference electrode 614 can be a metal combined with a metal salt such as an Ag/AgCl on-chip reference electrode. In another embodiment, the on-chip reference electrode can be a miniaturized electrode with a well-defined potential. In some embodiments, multiple sensors can share and use the same on-chip reference electrode 614. The on-chip reference electrode 614 can comprise a saturated calomel reference electrode (SCE) or a copper-copper (II) sulfate electrode (CSE). The on-chip reference electrode 614 can also comprise a pseudo-reference electrode including any metal that is not part of the active electrode such as platinum, silver, gold, or a combination thereof; any metal oxide or semiconductor oxide material such as aluminum oxide, iridium oxide, silicon oxide; or any conductive polymer electrodes such as polypyrrole, polyaniline, polyacetylene, or a combination thereof. In other embodiments, the on-chip reference electrode 614 can be covered by a miniaturized cell that stabilizes a small internal potential similar to a calomel electrode or an Ag/AgCl electrode.

Figure 7A:
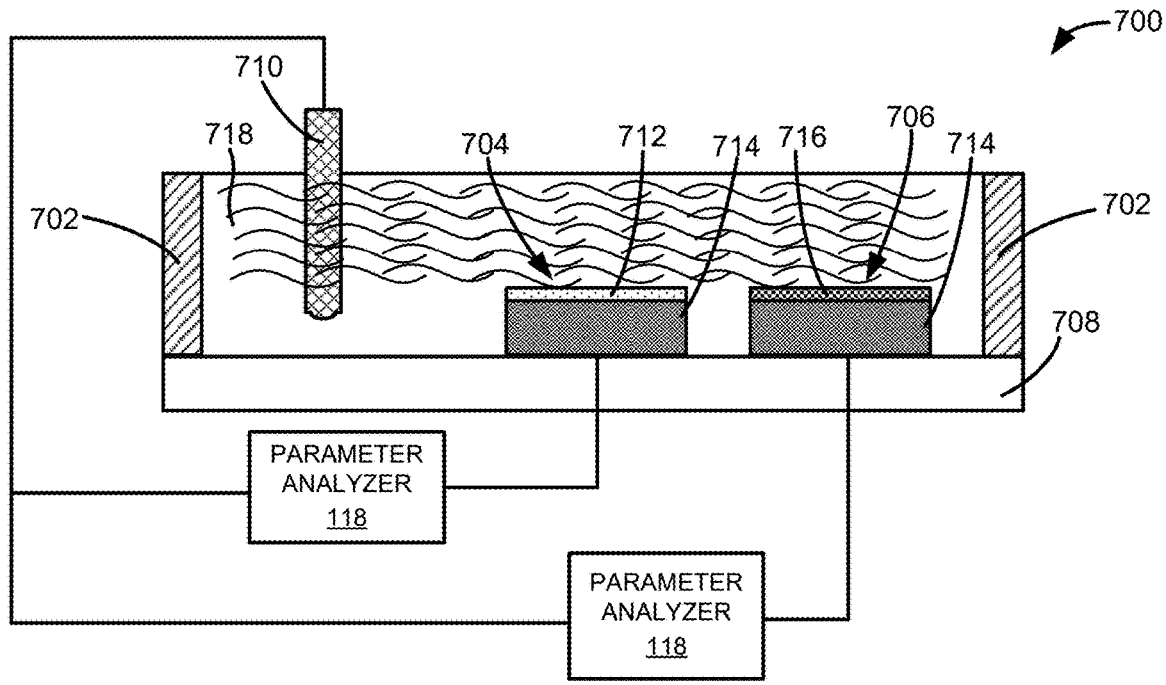
FIG. 7A illustrates a schematic of one embodiment of a combined ORP and pH sensor used as part of the methods and systems described herein.

FIG. 7A illustrates a schematic of one embodiment of a sensor 700 used as part of the methods and systems described herein. The sensor 700 of FIG. 7A can be or refer to any of the sensors 122 depicted in FIG. 1A, 1B, 2, 4A, or 4B. The sensor 700 can be or comprise an electrochemical cell having container walls 702, a first active electrode 704 and a second active electrode 706 positioned on a substrate layer 708, and an external reference electrode 710. Although two active electrodes are shown in FIG. 7A, it is contemplated by this disclosure and it should be understood by one of ordinary skill in the art that three or more active electrodes or multiple reference electrodes can be positioned on one substrate layer.

The first active electrode 704 can comprise a redox-active layer 712 disposed or otherwise positioned on a conductor layer 714. The second active electrode 706 can comprise a functionalization layer 716 disposed or otherwise positioned on a conductor layer 714. In some embodiments, the functionalization layer 716 can be a pH sensitive layer. In these and other embodiments, the first active electrode 704 can serve as part of an ORP sensor and the second active electrode 706 can serve as part of a pH sensor.

The container walls 702 of the sensor 700 can be configured to receive and retain a sampled solution 718. The container walls 702 can be made of an inert or non-conductive material. The container walls 702 can comprise, but is not limited to, a polymeric material such as polyvinyl chloride (PVC), poly(methyl methacrylate) (PMMA), polydimethylsiloxane (PDMS), a ceramic, glass, or a combination thereof.

In other embodiments not shown in the figures but contemplated by this disclosure, one or more layers of the sensor 700 can be in fluid contact or communication with the sampled solution 718 even though the sampled solution 718 is not retained within the container walls 702 of the sensor 700 or the sensor 700 has no container walls 702. The sampled solution 718 can be any of the diluted samples described herein or aliquots thereof.

As shown in FIG. 7A, one or more parameter analyzers 120 can be coupled to both the external reference electrode 710 and the conductor layers 714 of the first active electrode 704 and the second active electrode 706. The parameter analyzer 120 can be coupled to the external reference electrode 710 and the conductor layers 714 through one or more other layers of the sensor 700. The parameter analyzer 120 can be coupled to the first active electrode 704, the second active electrode 706, the external reference electrode 710, and any other active or reference electrodes and multiplex the signal from each of the electrodes in parallel or one after the other.

At least part of the external reference electrode 710 and the two active electrodes can be in fluid communication or in fluid contact with the sampled solution 718. As shown in FIG. 7A, at least part of the external reference electrode 710 can extend into or be immersed in the sampled solution 718. The sampled solution 718 can refer to any of the diluted samples 112, the reference samples 208, or aliquots thereof.

The external reference electrode 710 can also have a stable or well-known internal voltage and can also act as a differential noise filter for removing electrical noise from measurements taken using the sensor 700. In one embodiment, the external reference electrode 710 can be a stand-alone probe or electrode coupled to the parameter analyzer 120. In other embodiments, the external reference electrode 710 can be integrated with the parameter analyzer 120. As shown in FIG. 7A, the first active electrode 704 and the second active electrode 706 can be coupled to and share the same external reference electrode 710. Although FIG. 7A shows the first active electrode 704 and the second active electrode 706 coupled to separate parameter analyzers 120, it is contemplated by this disclosure and it should be understood by one of ordinary skill in the art that the first active electrode 704 and the second active electrode 706 can be coupled to the same parameter analyzer 120.

In one embodiment, the external reference electrode 710 can be or comprise a silver/silver chloride (Ag/AgCl) electrode. In other embodiments, the external reference electrode 710 can be or comprise a saturated calomel reference electrode (SCE) or a copper-copper (II) sulfate electrode (CSE). The external reference electrode 710 can also be a pseudo-reference electrode including any metal that is not part of the active electrode such as platinum, silver, gold, or a combination thereof; any metal oxide or semiconductor oxide material such as aluminum oxide, iridium oxide, silicon oxide; or any conductive polymer electrodes such as polypyrrole, polyaniline, polyacetylene, or a combination thereof.

As depicted in FIG. 7A, each of the first active electrode 704 and the second active electrode 706 can comprise at least one conductor layer 714 disposed or otherwise positioned on the substrate layer 708. The substrate layer 708 can comprise any non-conducting material such as a polymer, an oxide, a ceramic, or a composite thereof.

The conductor layer 714 can comprise a metal, a semiconducting material, a metal/metal-salt, or a combination thereof. For example, the conductor layer 714 can comprise silicon, gold, silver, aluminum, platinum, or a composite thereof. The conductor layer 714 can also be an organic semiconductor, a carbon nanotube, graphene, an organic conductor such as those derived from polyacetylene, polyaniline, Quinacridone, Poly(3,4-ethylenedioxythiophene) or PEDOT, PEDOT: polystyrene sulfonate (PSS), or a combination thereof. The conductor layer 714 can be composed of any conducting material which allows an electrical property change to be measured, including, but not limited to, a voltage change, a capacitance change, a conductance change, and/or a current change measured through the conductor layer 714, the redox-active layer 712 or the functionalization layer 716, and the sampled solution 718. The conductor layer 714 can also refer to multiple conductive layers such as a stack of metallic layers. For example, the metallic layers can comprise gold layers, platinum layers, or a combination thereof.

The first active electrode 704 can comprise a redox-active layer 712 or layer disposed or otherwise covering a conductor layer 714. The redox-active layer 712 can comprise a gold layer, a platinum layer, a metal oxide layer, a carbon layer, or a combination thereof on top of the conductor layer 714 (or multiple conductor layers 714). In some embodiments, the metal oxide layer can comprise an iridium oxide layer, a ruthenium oxide layer, or a combination thereof. In other embodiments, the conductor layer 714 can be the redox-active layer 712 and can comprise the gold layer, the platinum layer, the metal oxide layer, the carbon layer, or a combination thereof.

The parameter analyzer 120 (or another device coupled to the parameter analyzer 120, such as the computing device 116, not shown) coupled to the first active electrode 704 and the external reference electrode 710 can determine the ORP of the sampled solution 718 by measuring the potential difference between the external reference electrode 710 and the first active electrode 704.

In some embodiments, the parameter analyzer 120 can be a voltmeter or any other type of high-impedance amplifier or sourcemeter. The parameter analyzer 120 can measure a relative change in an equilibrium potential at an interface between the redox-active layer 712 and the sampled solution 718 containing the electro-active redox species. The parameter analyzer 120 can also measure a relative change in the equilibrium potential at an interface between the conductor layer 714 and the sampled solution 718 containing the electro-active redox species. The change in the equilibrium potential can be measured with respect to the external reference electrode 710. The parameter analyzer 120 can also be used to apply a voltage or current to the external reference electrode 710 or the active electrodes.

The solution characteristic of the sampled solution 718 can change as the amount of electro-active redox species changes due to the energy use, oxygen uptake or release, growth, or metabolism of the infectious agents in solution. For example, the amount of electro-active redox species in the sampled solution 718 can change as a result of cellular activity undertaken by the infectious agents in solution. As a more specific example, the amount of electron donors (e.g., the amount of energy carriers such as nicotinamide adenine dinucleotide (NADH) and flavin adenine dinucleotide ($FADH_2$)) in the sampled solution 718 can change due to the growth or lack thereof of the infectious agents in solution. Also, as another more specific example, the amount of oxygen depleted in the sampled solution 718 can change due to the growth or lack thereof of the infectious agents in solution.

The second active electrode 706 can comprise a functionalization layer 716 disposed or otherwise covering a conductor layer 714. The functionalization layer 716 can comprise oxides, silanes, DNA, proteins, antibodies, self-assembled mono layers (SAMs), oxides, buffered hydrogels, PVC, parylene, polyACE, or any other biochemically active materials. The functionalization layer 716 can be a pH-sensitive layer or pH-active layer configured to interact with ions, analytes, or other molecules or byproducts in the sampled solution 718. For example, the functionalization layer 716 can comprise hydroxyl groups which can interact with hydrogen ions ($H^+$) in the sampled solution 718.

The parameter analyzer 120 (or another device coupled to the parameter analyzer 120, such as the computing device 116, not shown) coupled to the second active electrode 706 and the external reference electrode 710 can determine the pH of the sampled solution 718 by measuring the potential difference between the external reference electrode 710 and the second active electrode 706.

The parameter analyzer 120 can measure a relative change in an equilibrium potential at an interface between the functionalization layer 716 and the sampled solution 718 containing the ions, analytes, or other molecules. The parameter analyzer 120 can also measure a relative change in the equilibrium potential at an interface between the conductor layer 714 and the sampled solution 718 containing the ions, analytes, or other molecules. The solution characteristic of the sampled solution 718 can change as the amount of ions, analytes, or other molecules changes due to the energy use, oxygen uptake or release, growth, or metabolism of the infectious agents in solution. For example, the amount of hydrogen ions (H±) in the sampled solution 718 can change as a result of cellular activity undertaken by the infectious agents in solution. The change in the equilibrium potential can be measured with respect to the external reference electrode 710. In these instances, what is measured by the parameter analyzer 120 (or the computing device 116 coupled to the parameter analyzer 120, not shown) is a relative change in the electrical characteristic of the sensor 700.

Figure 7B:
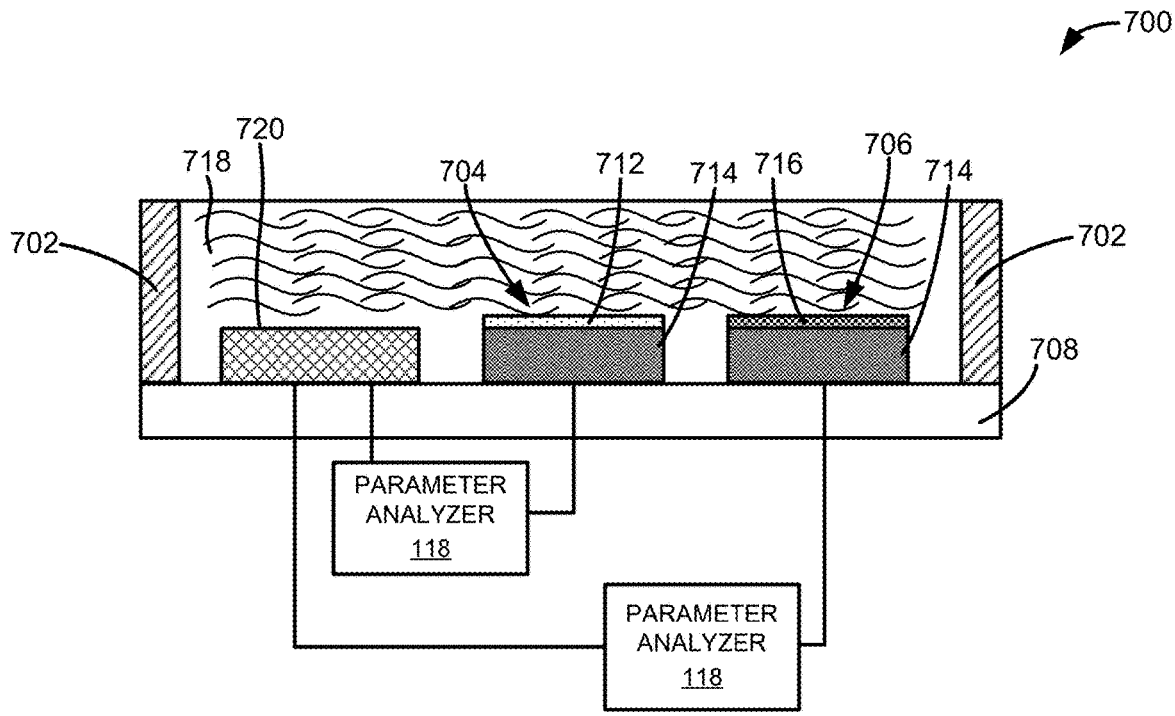
FIG. 7B illustrates a schematic of another embodiment of a combined ORP and pH sensor used as part of the methods and systems described herein.

FIG. 7B illustrates a schematic of another embodiment of the sensor 700 used as part of the methods and systems described herein. The sensor 700 of FIG. 7B can be or refer to any of the sensors 122 depicted in FIG. 1A, 1B, 2, 4A, or 4B.

The sensor 700 can be or comprise an electrochemical cell having container walls 702, a first active electrode 704 and a second active electrode 706 positioned on a substrate layer 708, and an on-chip reference electrode 720 positioned on the same substrate layer 708. Although two active electrodes are shown in FIG. 7B, it is contemplated by this disclosure and it should be understood by one of ordinary skill in the art that three or more active electrodes or multiple reference electrodes can be positioned on one substrate layer.

The container walls 702, the first active electrode 704, the second active electrode 706, and the substrate layer 708 of FIG. 7B can be the same as the container walls 702, the first active electrode 704, the second active electrode 706, and the substrate layer 708, respectively, of FIG. 7A. The sampled solution 718 can be in fluid communication or otherwise exposed to the on-chip reference electrode 720, the first active electrode 704, and the second active electrode 706 at the same time.

Although not shown in FIG. 7B, a passivation layer can be disposed on or cover the on-chip reference electrode 720. The passivation layer can be configured to prevent the on-chip reference electrode 720 from interacting with redox-active species, analytes, ions, or other molecules in the sampled solution 718. For example, the passivation layer can be a pH-insensitive layer. The passivation layer can comprise silanes, self-assembled monolayers (SAMs), buffered hydrogels, parylene, polyACE, or any other biochemically inert material.

In this embodiment, the parameter analyzer 120 can have a lead connection wire, such as a copper wire, coupled to the conductor layers 714 of the active electrodes and another lead connection wire connected to the on-chip reference electrode 720. The parameter analyzer 120 can be coupled to the first active electrode 704, the second active electrode 706, the on-chip reference electrode 720, and any other active or reference electrodes and multiplex the signal from each of the electrodes in parallel or one after the other. The parameter analyzer 120 can also be used to apply a voltage or current to the on-chip reference electrode 720 or the active electrodes.

In this and other embodiments, the sensor 700 shown in FIG. 7B miniaturizes the sensor set-up shown in FIG. 7A. The on-chip reference electrode 720 obviates the need for an external reference electrode, such as the external reference electrode 710. The on-chip reference electrode 720 can also be a silver/silver chloride (Ag/AgCl) electrode. In other embodiments, the on-chip reference electrode 720 can be, but is not limited to, a saturated calomel reference electrode (SCE) or a copper-copper (II) sulfate electrode (CSE). The on-chip reference electrode 720 provides similar functionality as that of the external reference electrode 710.

In one embodiment, a conductor layer 714 can be used as an on-chip reference electrode 720. The conductor layer 714 serving as the on-chip reference electrode 720 can be a metal covered with a metal salt such as a metal chloride. In another embodiment, the conductor layer 714 serving as the on-chip reference electrode 720 can also be covered with an oxide. For example, the conductor layer 714 can be a silver/silver chloride contact. In some embodiments, the conductor layer 714 can be covered by a passivation layer such as a KCL electrolyte gel or KCL solution to prevent the conductor layer 714 from interacting with redox-active species, analytes, ions, or other molecules in the sampled solution 718 and to act as a reference electrode. In other embodiments, the on-chip reference electrode 720 can be covered by a miniaturized cell that stabilizes a small internal potential like the calomel electrode.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. For example, the flowcharts or process flows depicted in the figures do not require the particular order shown to achieve the desired result. Moreover, additional steps or operations may be provided or steps or operations may be eliminated to achieve the desired result.

It will be understood by one of ordinary skill in the art that all or a portion of the methods disclosed herein may be embodied in a non-transitory machine readable or accessible medium comprising instructions readable or executable by a processor or processing unit of a computing device or other type of machine.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure. The scope of the present invention is limited only by the appended claims.

What is claimed is:

1. A method of preparing an output sample of a bacteria of a defined concentration, comprising:
   identifying a species of the bacteria within a source sample;
   diluting an aliquot of the source sample comprising the bacteria by a dilution factor to yield a diluted sample, wherein the aliquot is diluted using a dilutive solution;
   selecting a look-up table based on the species of the bacteria; wherein the look-up table contains concentration data;
   selecting a first threshold amount and a second threshold amount from the look-up table, wherein the first threshold amount and the second threshold amount are target amounts by which an oxidation-reduction potential (ORP) of the diluted sample is required to change in order for the concentration of the bacteria in the diluted sample to reach the defined concentration, wherein the defined concentration is between $5 \times 10^5$ colony-forming units (CFU)/mL to $3 \times 10^8$ CFU/mL, wherein the first threshold amount and the second threshold amount comprise different values;
   exposing one or more ORP sensors to the diluted sample, wherein each of the one or more ORP sensors comprises an active electrode and a reference electrode, wherein at least a redox-active layer of the active electrode of each of the one or more ORP sensors is in fluid communication with the diluted sample when exposed to the diluted sample;
   incubating the diluted sample at an incubation temperature, wherein the diluted sample is incubated when the one or more ORP sensors are exposed to the diluted sample;
   incubating the diluted sample at an incubation temperature, wherein the diluted sample is incubated when the one or more ORP sensors are exposed to the diluted sample;
   measuring, using a parameter analyzer coupled to the one or more ORP sensors, a change in an ORP of the diluted and incubated sample, wherein the change in the ORP is measured between the redox-active layer of the active electrode and the reference electrode;
   obtaining, using the parameter analyzer or a computing device communicatively coupled to the parameter analyzer, a first threshold time corresponding to an amount of time elapsed for the ORP of the diluted and incubated sample to change by the first threshold amount and obtaining a second threshold time corresponding to the amount of time elapsed for the ORP of the diluted and incubated sample to change by the second threshold amount, wherein the first threshold amount and the second threshold amount represent changes in the ORP of the diluted and incubated sample;
   determining, using the parameter analyzer or a computing device communicatively coupled to the parameter analyzer, a sample preparation time corresponding to the amount of time necessary for the bacteria within the diluted and incubated sample to reach the defined concentration based on the first threshold time, the second threshold time, concentration data from the look-up table, and the defined concentration; and cooling the diluted and incubated sample to a cooling temperature between about 4° C. and about 25° C. when the sample preparation time is reached.

2. The method of claim 1, wherein the look-up table is a species-specific look-up table, wherein the species-specific look-up table is generated from multiple strain-specific look-up tables representing data obtained from multiple reference samples monitored over time, and wherein each of the multiple reference samples comprises a reference bacteria of the same species as the bacteria in the source sample.

3. The method of claim 2, wherein each of the multiple strain-specific look-up tables is generated by:
measuring changes in the ORP of a reference sample over a period of time;
conducting sample enumeration assays of the reference sample over the same period of time;
converting results of the sample enumeration assays to reference sample concentrations using a conversion factor; and
associating the reference sample concentrations with the changes in the ORP of the reference sample.

4. The method of claim 3, wherein the species-specific look-up table is generated by taking an average of all ORP change amounts obtained from the multiple strain-specific look-up tables for each of the reference sample concentrations and associating each of the reference sample concentrations with an averaged ORP change amount.

5. The method of claim 3, wherein the sample enumeration assays comprise optical density measurements, plate count assays, flow cytometry assays, or a combination thereof.

6. The method of claim 1, wherein the incubation temperature is between about 33° C. and about 37° C.

7. The method of claim 1, further comprising diluting the output sample by another dilution factor to yield a further diluted sample, wherein the further diluted sample comprises a bacterial concentration required for downstream testing.

8. The method of claim 1, wherein the redox-active layer comprises a gold layer, a platinum layer, a metal oxide layer, a carbon layer, or a combination thereof.

9. The method of claim 1, wherein the source sample comprises a bodily fluid, a wound swab or sample, a rectal swab or sample, a culture derived therefrom, or a combination thereof.

10. The method of claim 9, wherein the bodily fluid comprises urine, blood, sputum, saliva, breast milk, spinal fluid, semen, vaginal secretions, synovial fluid, pleural fluid, peritoneal fluid, pericardial fluid, amniotic fluid, cultures of bodily fluid that have tested positive for bacterial growth, or a combination thereof.

* * * * *